(12) United States Patent
Gorenstein et al.

(10) Patent No.: US 9,988,623 B2
(45) Date of Patent: Jun. 5, 2018

(54) METHODS OF X-APTAMER GENERATION AND COMPOSITIONS THEREOF

(71) Applicants: Board of Regents of the University of Texas System, Austin, TX (US); AM Biotechnologies, LLC, Houston, TX (US)

(72) Inventors: David G Gorenstein, Houston, TX (US); Weiguo He, Pearland, TX (US); David E Volk, Dickinson, TX (US); Miguel-Angel Elizondo-Riojas, Houston, TX (US); Ross Durland, The Woodlands, TX (US); Johnnie Engelhardt, West Columbia, TX (US)

(73) Assignees: AM Biotechnologies, LLC, Houston, TX (US); Board of Regents of the University of Texas System, Austin, TX (US)

( * ) Notice: Subject to any disclaimer, the term of this patent is extended or adjusted under 35 U.S.C. 154(b) by 1137 days.

(21) Appl. No.: 14/051,363

(22) Filed: Oct. 10, 2013

(65) Prior Publication Data
US 2014/0100120 A1    Apr. 10, 2014

Related U.S. Application Data

(60) Provisional application No. 61/711,915, filed on Oct. 10, 2012.

(51) Int. Cl.
*C12N 15/115* (2010.01)
*C12N 15/10* (2006.01)

(52) U.S. Cl.
CPC ..... *C12N 15/1058* (2013.01); *C12N 15/1048* (2013.01); *C12N 15/115* (2013.01); *C12N 2310/16* (2013.01); *C12N 2310/315* (2013.01); *C12N 2310/351* (2013.01); *C12N 2320/11* (2013.01); *C12N 2330/31* (2013.01)

(58) Field of Classification Search
None
See application file for complete search history.

(56) References Cited

U.S. PATENT DOCUMENTS

| | | | |
|---|---|---|---|
| 6,423,493 | B1 | 7/2002 | Gorenstein et al. |
| 7,338,762 | B2 | 3/2008 | Gorenstein et al. |
| 7,576,037 | B2 | 8/2009 | Engelhardt et al. |
| 2005/0123939 | A1 * | 6/2005 | Gorenstein ........ G01N 33/6851 506/6 |

OTHER PUBLICATIONS

Adamczyk et al (2003 Tetrahedron 59:5749-61).*
Banerji S., et al. "Characterization of a functional hyaluronan-binding domain from the human CD44 molecule expressed in *Escherichia coli*" Protein Expression and Purification 14 (1998) 371-381.
Brody EN, et al. "High-content affinity-based proteomics: unlocking protein biomarker discovery" Expert Rev Mol Diagn 10 (2010) 1013-22.
Ellington and Szostak. "In vitro selection of RNA molecules that bind specific ligands" Nature 346 (1990) 818-822.
Keefe AD, Cload ST "SELEX with modified nucleotides" Current Opinion in Chemical Biology 12 (2008) 448-456.
Lang et al. "Dock 6: Combining techniques to model RNA—small molecule complexes" RNA 15 (2009) 1219-1230.
Shuker et al. "Discovering High-Affinity Ligands for Proteins: SAR by NMR" Science 274 (1996) 1531-1534.
Somasunderam A et al. "Combinatorial Selection of DNA Thioaptamers Targeted to the HA Binding Domain of Human CD44" Biochemistry 49 (2010) 9106-9112.
Tuerk and Gold "Systematic Evolution of Ligands by Exponential Enrichment: RNA Ligands to Bacteriophage T4 DNA Polymerase" Science 249 (1990) 505-510.
Yang X; Li N; Gorenstein DG "Strategies for the discovery of therapeutic Aptamers" Expert Opin Drug Discov 6 (2011) 75-87.
Yang, X. et al. "Construction and selection of bead bound combinatorial oligonucleoside phosphorothioate and phosphorodithioate aptamer libraries designed for rapid PCR-based sequencing" Nucleic Acids Research 30 (2002) e132.
Yang, X. et al. "Immunofluorescence assay and flow-cytometry selection of beadbound aptamers" Nucleic Acids Research 31 (2003) e54.
Zuker, M. "Mfold web server for nucleic acid folding and hybridization prediction" Nucleic Acids Research 31 (2003) 3406-3415.

* cited by examiner

*Primary Examiner* — Christopher M Gross
(74) *Attorney, Agent, or Firm* — Blank Rome LLP

(57) ABSTRACT

Provided herein are methods for a novel bead-based next-generation "X-aptamer" selection scheme that extends aptamer technology to include X-modified bases, thus resulting in X-aptamers, at any position along the sequence because the aptamers are chemically synthesized via a split-pool scheme on individual beads. Also provides are application to a wide range of commonly used DNA modifications, including, but not limited to, monothioate and dithioate backbone substitutions. This new class of aptamer allows chemical modifications introduced to any of the bases in the aptamer sequence as well as the phosphate backbones and can be extended to other carbohydrate-based systems.

17 Claims, 20 Drawing Sheets

Figure 1A

Pre-selected Aptamers – 5' monothiolated at each A

| Name | Sequence of selected XAs | SEQ ID |
|---|---|---|
| TA1 | 5'-PRIMER-CCAA-GGCC-TGC-AAG-GGA-ACC-AAG-GAC-AC-AG-PRIMER-3' | 1 |
| TA2 | 5'-PRIMER-CCAA-GGCA-TGC-AAG-GGA-ACC-AAG-GAC-AC-AG-PRIMER-3' | 2 |
| TA3 | 5'-PRIMER-TGCA-GATG-CAA-GGT-AAC-CAT-ATC-CAA-AG-CA-PRIMER-3' | 3 |
| TA4 | 5'-PRIMER-CGTA-TGCA-AGG-TGA-AAG-CAG-CAC-ACC-AA-TA-PRIMER-3' | 4 |
| TA5 | 5'-PRIMER-GCGG-CAGT-AGT-TGA-TCC-CGA-AGC-GTT-AC-GA-PRIMER-3' | 5 |
| TA6 | 5'-PRIMER-TTGG-GACG-GTG-TTA-AAC-GAA-AGG-GGA-CG-AC-PRIMER-3' | 6 |

Figure 1B

Column Program using fully thiolated nucleotides

| Name | Sequence of selected XAs | SEQ ID |
|---|---|---|
| CL1 | 5'-PRIMER-CCAA*GGCC*TGC*AAG*GGA*ACC*AAG*GAC*AC*AG-PRIMER-3' | 7 |
| CL2 | 5'-PRIMER-XGCA*GATC*CAG*TAG*GTA*XCC*ATA*TCC*AA*TA-PRIMER-3' | 8 |
| CL3 | 5'-PRIMER-TTGG*GACG*XGX*TAA*ACG*AAG*GGG*ACG*GT*GA-PRIMER-3' | 9 |
| CL4 | 5'-PRIMER-XXAA*GAXA*CAX*AAX*XGA*AXG*XAA*XAC*AX*XG-PRIMER-3' | 10 |

Resulting theoretical X-Aptamer showing column path (from 3' to 5') 3-4-2-4-1-3-2-4-2-1

| Name | Sequence of Exemplary XAs | SEQ ID |
|---|---|---|
| EX | 5'-PRIMER CCAA GATC CAX TAG ACG ACC XAA TCC AX GA PRIMER-3' | 11 |

Figure 1C

Isolated X-Aptamers

| Name | Sequence of selected XAs | SEQ ID |
|---|---|---|
| XA1 | 5'-PRIMER-XXAA-GATC-XGX-TAG-GGA-ACC-AAG-ACG-AC-AG-PRIMER-3' | 12 |
| XA2 | 5'-PRIMER-XGCA-GATC-TGC-AAG-GGA-ACC-AAG-GAC-AC-TA-PRIMER-3' | 13 |
| XA3 | 5'-PRIMER-CCAA-GGCC-TGC-AAG-GGA-ACC-AAG-TCC-AX-TA-PRIMER-3' | 14 |
| XA4 | 5'-PRIMER-TTGG-GGCC-TGC-AAG-ACG-XCC-ATA-GAC-AC-AG-PRIMER-3' | 15 |
| XA5 | 5'-PRIMER-XGCA-GAXA-CAG-TAA-ACG-XCC-ATA-GAC-AC-AG-PRIMER-3' | 16 |
| XA6 | 5'-PRIMER-TTGG-GGCC-TGC-AAG-ACG-ACC-XAA-ACG-AX-GA-PRIMER-3' | 17 |
| XA7 | 5'-PRIMER-XXAA-GACG-CAX-TAA-XGA-ACC-AAG-GAC-GT-GA-PRIMER-3' | 18 |
| XA8 | 5'-PRIMER-CCAA-GATC-XGX-AAG-GTA-XCC-GGG-GAC----XG-PRIMER-3' | 19 |
| XA9 | 5'-PRIMER-XXAA-GATC-TGC-AAX-GTA-ACC-ATA-GAC-AC-AG-PRIMER-3' | 20 |
| XA10 | 5'-PRIMER-TTGG-GGCC-CAG-TAG-GTA-ACC-GGG-GAC----AG-PRIMER-3' | 21 |
| XA11 | 5'-PRIMER-TTGG-GACG--------TAA-GTA-AXG-GGG-GAC-AX-GA-PRIMER-3' | 22 |
| XA12 | 5'-PRIMER-XXAA-GGCC-XGX-TAA-----AXG-ATA-TCC-AC-TA-PRIMER-3' | 23 |
| XA13 | 5'-PRIMER-XGCA-GATC-TGC-AAG-GGA-AAG-ATA-GAC-AC-AG-PRIMER-3' | 24 |

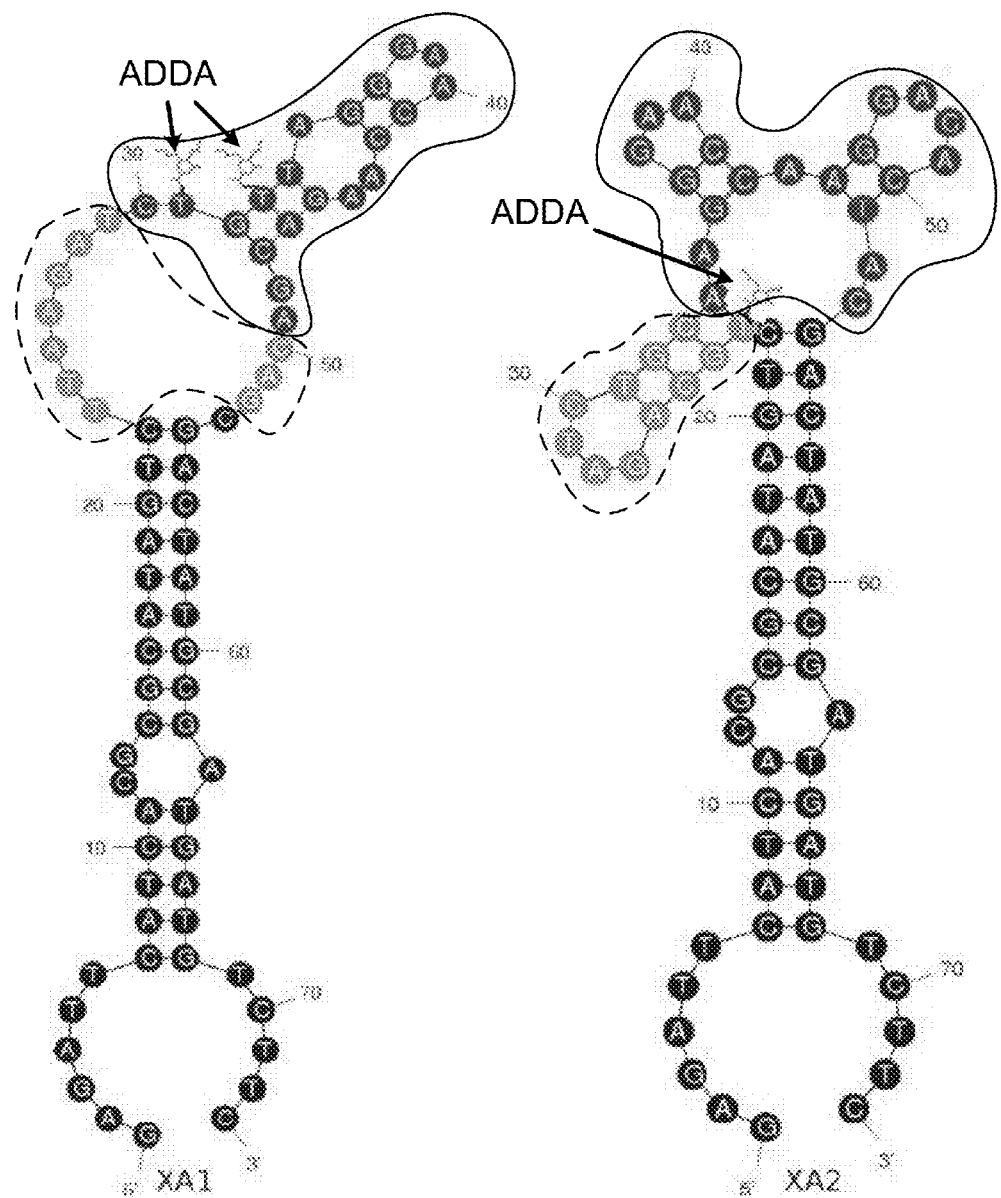

"Click chemistry" in which azide and alkyne combine in presence of copper to form a triazole Figure 13
X-Aptamers: Base Modifications with Novel Chemical Functionalities
A 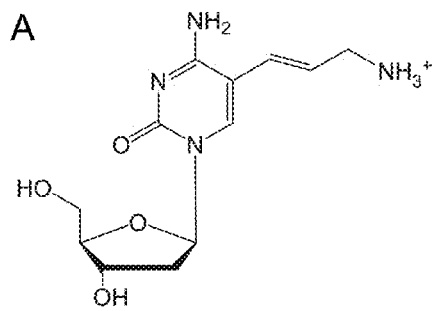
B 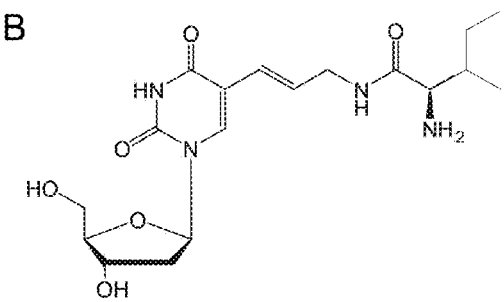
C 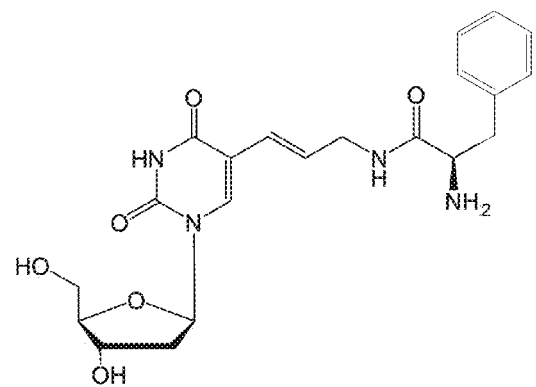
D 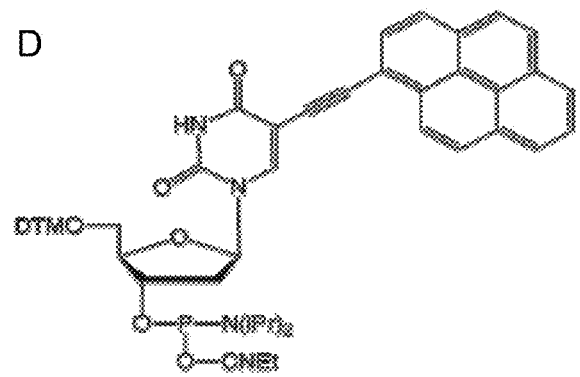

Figure 21A

| | | |
|---|---|---|
| Motif1 | AAGGGAACCAAGGACACTAC (CD44-ADDA) | SEQ ID 58 |
| CD44-PA: | | |
| 2570 | XXAAGACGXGXAAGGGAACCAAGGACACTA | SEQ ID 59 |
| 182 | T-AAGACGXGXAAGGGAACCAAGGACACTA (T-AA -> XXAA) | SEQ ID 60 |

| | | |
|---|---|---|
| Motif2 | CXGXTAGGGAACCAAGACGA (CD44-ADDA) | SEQ ID 54 |
| CD44-PA: | | |
| 4672 | CCAAGACGXGXTAAGGAACCAAGACGACTA | SEQ ID 61 |
| 9 | CCAAGACGXGXTAGGGAACCAAGACGACTA (G -> A) | SEQ ID 62 |

| | | |
|---|---|---|
| Motif3 | GCCTGCAAGACGXCCATAGACAC (CD44-ADDA) | SEQ ID 55 |
| CD44-PA: | | |
| 3 | TTGGGGCCTGCAAGACGXCCATAGACACAG | SEQ ID 63 |

| | | |
|---|---|---|
| Motif4 | GATCTGCAAXGTAACCATAGACA (CD44-ADDA) | SEQ ID 56 |
| CD44-PA: | | |
| 1 | XXAAGATCTGCAAXGTAACCATAGACACAG | SEQ ID 64 |

| | | |
|---|---|---|
| Motif5 | AGAXACAGTAAACGXCCATAGACAC (CD44-ADDA) | SEQ ID 57 |
| CD44-PA: | | |
| 3068 | XXAAGATCCAGTAGACGXCCATAXACAXTA | SEQ ID 65 |
| 104 | T-AAGATCCAGTAGACGXCCATAXACAXTA | SEQ ID 66 |
| 5 | XGCAGAXACAGTAAACGXCCATAGACACAG | SEQ ID 67 |

Figure 21B

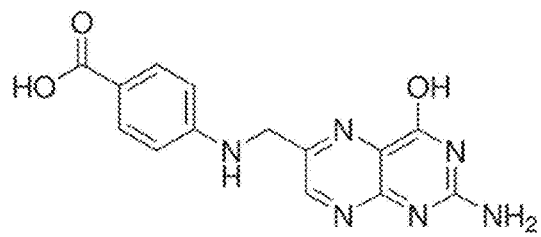

METHODS OF X-APTAMER GENERATION AND COMPOSITIONS THEREOF

CROSS REFERENCE TO RELATED APPLICATIONS

This application claims priority based on U.S. Provisional Application Ser. No. 61/711,915 filed Oct. 10, 2012, which is incorporated herein by reference.

STATEMENT REGARDING GOVERNMENT INTERESTS

This invention was made with Government support under HHSN272200800048C, HHSN268201000037C, CA151668, HD080020, AI054827, 275200800020C, and GM092599 awarded by The National Institutes of Health and under W81XWH-09-1-0212 and W81XWH-09-2-0139 awarded by The Department of Defense. The Government has certain rights in the invention.

FIELD OF THE INVENTION

This invention relates generally to methods for selection of aptamers having small molecule substituents. The present invention relates more particularly to combining random or pseudo-random bead-based aptamer libraries with conjugation chemistry to produce modified aptamers having enhanced chemical functionality.

BACKGROUND OF THE INVENTION

Without limiting the scope of the invention, its background is described in connection with aptamers generally and traditional aptamer generation methodologies.

Aptamers are structurally distinct RNA and DNA oligonucleotides (ODNs) that can mimic protein-binding molecules and exhibit high (nM) binding affinity based on their unique secondary three-dimensional structure conformations and not by pair-wise nucleic acid binding. Aptamers can be selected via high-throughput in vitro methods to bind target molecules. Aptamers are thus emerging as viable alternatives to small molecules and antibody-based therapies in the field of drug development.

Aptamers are typically approximately 1/10th the molecular weight of antibodies and yet provide complex tertiary, folded structures with sufficient recognition surface areas to rival antibodies. However, aptamers achieve their selectivity through a very limited repertoire of functional groups—the sugar phosphate backbone and 4 bases. In contrast antibodies use all 20 amino acids with a full range of chemical substituents including positively-charged, sulfhydryl, hydrophobic sidechains, etc. Aptamers are polyanions, potentially limiting their affinity towards the full diversity of proteins. It is often difficult to select an aptamer targeted to very acidic proteins because there are no cationic groups to neutralize anionic surfaces on the protein. While oligonucleotide agents show therapeutic promise, various pharmacological problems must be overcome. High sensitivity to nuclease digestion makes oligonucleotide agents unstable and thus impracticable for in vivo administration by either intravenous or oral routes.

In fact, a diverse range of modifications at all possible modification sites of an oligonucleotide have been reported for enhancing oligonucleotide drug properties including in vivo stability. These include alterations of linkages (backbones), heterocycles, carbohydrates, and connection and conjugation sites, as well as the complete removal of the sugar-phosphate backbone. See, e.g. Yang X; Li N; Gorenstein D G *Expert Opin Drug Discov* 6 (2011) 75-87; Brody E N, et al. *Expert Rev Mol Diagn* 10 (2010) 1013-22; Keefe A D, Cload S T *Current Opinion in Chemical Biology* 12 (2008) 448-456.

Certain of the present inventors have developed thiophosphate-backbone modified aptamers ("thio" aptamers) as specific protein-binding reagents that are endowed with nuclease resistance. See, e.g. Yang, X. et al. *Nucleic Acids Research* 30 (2002) e132; Yang, X. et al. *Nucleic Acids Research* 31 (2003) e54. Oligonucleotides with high monothio- or dithiophosphate backbone substitutions enhance the specificity and affinity of these agents for the desired protein target and also enhance the nuclease stability.

However effort to combine the best attributes of antibodies, small molecules and aptamers has remained elusive. Selection of aptamers by the classical iterative selection-amplification method followed by post-selection modification has been disappointing because the modifications affect the three dimensional structure of the aptamer, which is the basis of its ability to bind to the target by which it was selected. It has been shown that certain substituents can be introduced into the bases of the oligonucleotides to provide additional functionalities. For instance, the 5-position of dU can be replaced with a range of substituents (X) and still allow Taq and other polymerases to amplify the selected sequences. Thus, with the appropriate 5-X-dUTP, it is possible to amplify a selected sequence during the in vitro iterative SELEX scheme and create a large initial random library ($10^{14}$ different sequences), then select a subset that binds to the target protein, amplify and repeat this cycle—often 10-15 cycles are required. The problem is that every 5-X-dU position will have the same modified X-substituent.

From the foregoing it is apparent there is a need in the art for robust methods that allow the selection of modified aptamers having desired chemical substituents. The invention described herein provides novel methods for achieving this end.

BRIEF SUMMARY OF THE INVENTION

Disclosed herein are methods for a novel bead-based next-generation "X-aptamer" selection scheme that extends aptamer technology to include X-modified bases (thus resulting in X-aptamers) at any position along the sequence because the aptamers are chemically synthesized via a split-pool scheme on individual beads. As used herein, the term X-aptamer refers to a subclass of aptamers that have as a part of their sequence chemically modified oligonucleotides that are not the substrate of a polymerase enzyme. As such, X-aptamers cannot be generated by an iterative SELEX type selection but must be selected from one-bead libraries generated by split and pool synthesis. This new technology is compatible with a wide range of commonly used DNA modifications, including, but not limited to, monothioate and dithioate backbone substitutions. This is a new class of aptamer, where any chemical modifications can be introduced to any of the bases as well as the phosphate backbones and could be extended to other carbohydrate-based systems.

In one embodiment a system is provided for identifying both novel X-aptamer affinity agents that feature small molecule X-group modifications on the bases and may (or may not) contain partially or fully modified phosphate backbones using a bead-based combinatorial library of X-aptamers as well as one or more target molecules that interact with a specific X-aptamer. The system includes use of a partially or fully-modified oligonucleotide-bead X-aptamer combinatorial library with small molecule X-group modifications on the bases for binding one or more target molecules, wherein each bead of the X-aptamer oligonucleotide-bead library comprises more than one copy of a unique oligonucleotide having a unique sequence and backbone and base modification(s). Target molecules may include proteins, peptides, carbohydrates, small molecules, intact cells, virions, etc. In certain embodiments, the modified backbones include monothioate and dithioate backbone substitutions.

In one embodiment a method for isolating a target specific X-aptamer is provided that includes the steps of generating an oligonucleotide library containing a plurality of different oligonucleotide sequences using bead based split and pool synthesis wherein at least one chemical linker derivitized nucleotide is pseudo-randomly inserted into the oligonucleotide sequences and wherein the chemical linker provides for attachment of an X-ligand into the oligonucleotide sequences thereby forming an X-aptamer library, and identifying a target specific X-aptamer sequence by target binding and sequence determination. In certain embodiments the oligonucleotide library is partially thio-modified or fully thio-modified. The unmodified oligonucleotide version of the target specific X-aptamer can be determined by nucleic acid sequencing or can be determined by polymerase chain reaction (PCR) amplification. The sequence serves as a sequence barcode for determining a step of the split and pool synthesis at which a chemically modified base was inserted.

The X-ligands can be attached to the chemical linker prior to creation of the oligonucleotide library, between split and pool steps during creation of the oligonucleotide library or after generation of the X-aptamer library. The X-ligands can be pre-coupled to one or more phosphoramidites used to synthesize the oligonucleotide library.

In certain embodiments a combinatorial X-aptamer oligonucleotide library on bead supports is generated from which target specific X-aptamers are isolated by target binding. The library can be generated by a process including the steps of:
  a) establishing a reaction column for each subunit oligonucleotide base species that will be used to synthesize a random collection of oligonucleotide sequences with modified base and/or backbones and distributing a set of activated or prederivitized supports in each reaction column;
  b) attaching a single nucleotide species to the supports in each of the columns wherein the single nucleotide species comprises a backbone substituted with a protected normal phosphate ester or a modified phosphate ester that is not a substrate for a polymerase enzyme and/or wherein a base of the single nucleotide species is unmodified or modified with a chemical linker that provides for attachment of an X-ligand to the oligonucleotide;
  c) mixing the supports from the columns together;
  d) splitting the mixed supports back into each of the columns; and
  e) repeating steps b)-d) until an oligonucleotide of a desired length is obtained, wherein each support comprises many copies of a unique X-aptamer oligonucleotide sequence, wherein each unique sequence contains at least one nucleotide species including a modified phosphate ester that is not a substrate for a polymerase enzyme and/or at least one nucleotide species that is modified with a chemical group X.

The aforementioned library can be generated where the X-ligands have been previously chosen to bind to a target molecule by in silico molecular modeling and the rest of the X-aptamer oligonucleotide serves as a scaffold to present one or more small-molecule X-ligands to bind to the target molecule. In certain embodiments, the subunit oligonucleotide base species are phosphoramidites or thiophosphoramidites and the X-ligands have been previously attached to the precursor phosphoramidites or thiophosphoramidites. The X-ligands may be attached by chemical process known to those of skill in the art including by "click chemistry" or amide coupling chemistry.

In certain embodiments, the process of adding the X-ligand begin with a predetermined or established aptamer or X-aptamer sequence.

Target specific X-aptamers are isolated from the combinatorial X-aptamer oligonucleotide library by selection of X-aptamers that specifically interact with a desired target. The sequences of the target specific X-aptamers are obtained. In one embodiment a nucleic acid sequencer is used to determine the sequence of the modified oligonucleotide with random X-group modifications on the bases (X-aptamer). Alternatively, oligonucleotides with random X-group modifications on the bases are PCR amplified to generate an unmodified version of the oligonucleotide and either sequenced directly or cloned prior to sequencing. Modification of the base with the X-group will still allow PCR amplification, albeit with an unmodified sequence that then serves as a barcode for the bead and later allows identification of the X-modifications and backbone modifications. The X-groups may have been previously chosen by any of a number of methods, including without limitation, groups predicted to bind to the target molecule by in silico molecular modeling, groups identified by high-throughput chemical screens, and/or using SAR by NMR ("structure-activity-relationships" by NMR) studies of small molecules libraries. The X-aptamer oligonucleotide serves as a scaffold to present one or more small-molecule X-groups to bind to the target molecule.

In certain embodiments, a protein separator is included that separates a bound protein into fragments prior to separation by liquid chromatography followed by mass spectrometry. The one or more proteins bound to the oligonucleotide X-aptamer may be extracted and separated prior to identifying the proteins using liquid chromatography, mass spectrometry (MS), liquid chromatography, and/or time of flight (TOF) mass spectrometry and combinations thereof.

In certain embodiments the oligonucleotides are attached to the supports using a chemical linker that is not cleaved upon oligonucleotide deprotection. Heat- or light-sensitive linkers attaching the X-aptamer to the bead may also be used.

In certain embodiments of the bead based library, the X-groups have been previously attached to the precursor phosphoramidites or thiophosphoramidites or the X-groups are attached between split and pool steps by "click chemistry" or amide-carboxyl coupling chemistry or by these and other coupling steps at the completion of the random library creation using bases incorporating such groups as azide or ethynyl X-groups (allowing for click chemistry), or carboxyl or amine groups (allowing for amide coupling chemistry).

BRIEF DESCRIPTION OF THE DRAWINGS

For a more complete understanding of the present invention, including features and advantages, reference is now made to the detailed description of the invention along with the accompanying figures:

FIG. 1A shows the sequences of preselected aptamers. FIG. 1B shows the sequences programmed into the synthesizer. CL1-CL4 represents the synthesis sequences programmed into the four-column synthesizer. Pool and split steps are indicated by asterisks. The resulting library consists of 1,048,576 ($4^{10}$) possible sequences. An example of one possible X-aptamer sequence from the library is shown, representing a bead that starts (from the 3' end) in column 3, and then is transferred in successive pool and split steps (3' to 5') to columns 4, 2, 4, 1, 3, 2, 4, 2, 1 (underlined sequence blocks). FIG. 1C shows the sequences of obtained X-aptamers.

FIGS. 4A-C illustrate the predicted secondary structures of selected XA sequences.

FIGS. 13A-D depict structures of certain exemplary base modifications for use in XA.

FIG. 21A presents the sequences of X-aptamers isolated for CD44 binding with a pteroic acid moiety attached.

FIG. 21B structure of pteroic acid.

DETAILED DESCRIPTION OF THE INVENTION

Figure 2A:
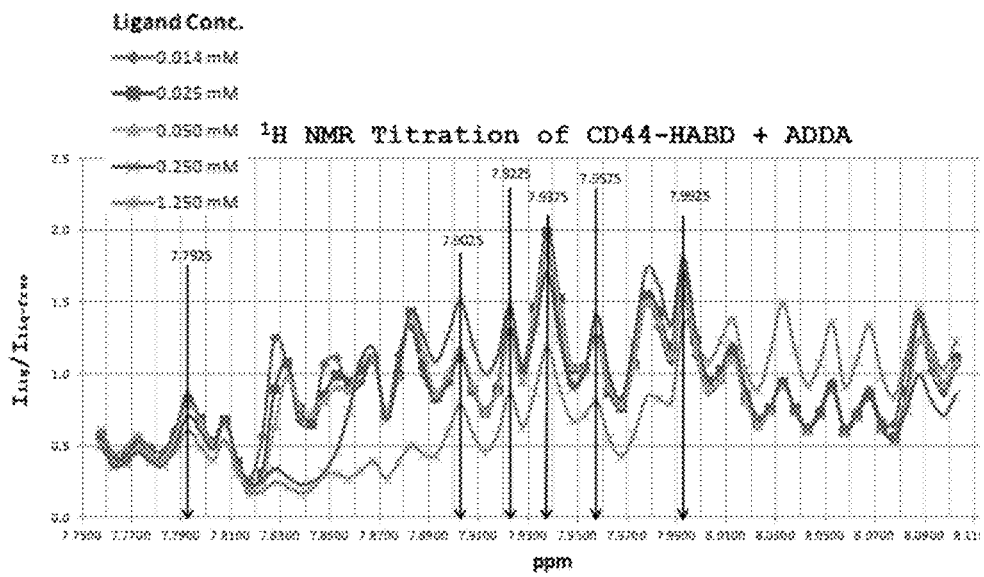
FIG. 2A shows a set of NMR spectra measured for CD44-HABD in the presence of different concentrations of the ADDA ligand titration of CD44-HABD.

While the making and using of various embodiments of the present invention are discussed in detail below, it should be appreciated that the present invention provides many applicable inventive concepts which can be employed in a wide variety of specific contexts. The specific embodiments discussed herein are merely illustrative of specific ways to make and use the invention and do not delimit the scope of the invention.

ABBREVIATIONS: The following abbreviations are used throughout this application:
5-$NH_2$-dU 5-(aminoethyl-3-acrylimido)-deoxyuridine
ADDA N-acetyl-2,3-dehydro-2-deoxyneuraminic acid
amino-dU 5-(aminoethyl-3-acrylimido)-deoxyuridine
CD44-HABD hyaluronic acid binding domain of CD44
ODN Oligodeoxynucleotide
PCR Polymerase Chain Reaction
SAR by NMR Structure-Activity-Relationships determined by Nuclear Magnetic Resonance (NMR)
SELEX Systematic Evolution of Ligands by Exponential Enrichment
TA Thio-aptamer
TBTA tris(benzyltriazolylmethyl)amine
XA X-aptamer To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

For purposes of the present invention, the acronym "SELEX" refers to the iterative selection and amplification aptamer selection method described in 1990 by Tuerk and Gold (*Science* 249 (1990) 505-510) and Ellington and Szostak (*Nature* 346 (1990) 818-822). As originally described, SELEX begins with a library of soluble oligonucleotides that is contacted with target compounds followed by partitioning of those nucleic acids having an increased affinity to the target from the candidate mixture. The partitioned nucleic acids are amplified by PCR and, in an iterative series of selection and amplification steps, enrichment and isolation of specific high affinity aptamers is obtained. See, e.g. Gold and Tuerk, U.S. Pat. No. 5,270,163, describing an in vitro combinatorial method for the identification of nucleic acid ligands.

Combinatorial chemistry involves linking together, in an essentially step-wise fashion, identical or non-identical building blocks such as monomeric subunits, chemical groups, and the like, to form libraries of new compounds. The term "library" as used herein refers to a collection of different individual molecules that have a common generic structure and are produced by combinatorial chemistry. Preferably, the library is designed to contain significant if not nearly equal representation of all possible different individual molecules that can be theoretically generated given the chemistry and added constituents. The term "library" in the context of the present invention also refers to the products of split combinatorial synthesis of organic molecules having a common core structure or template which has a discrete number of independently variable substituents, each of which can have one of a defined range of values. Such templates may have a number of different functional sites, including those where each site is amenable to a different coupling chemistry and where a plurality of different substituents are introduced for binding to a different site at succeeding coupling steps.

Aptamers constitute one class of oligonucleotide molecules derived from combinatorial chemistry. Aptamers are oligonucleotides (double or single stranded DNA or RNA molecules) that fold into sequence dependent three dimensional structures and are biologically active on the basis of resulting structure based interactions (such as decoys) or catalytic properties (such as antisense, ribozymes or siRNA). Identifying useful aptamers, or oligonucleotides having biologic activity on the basis of tertiary structure, requires the generation of large candidate libraries of random sequence or backbone modification oligonucleotides as well as selection, identification and reproduction of the rare structures that are able to interact with a given template. Identification of aptamer structures in libraries of oligonucleotides having regions of defined sequence as well as randomized sequence and backbone modifications such as thioaptamers can be performed by in vitro selection and amplification by PCR.

The bead-based split synthesis selection process disclosed and utilized herein is distinct from the above referenced SELEX methodology. Split synthesis as originally adapted to generation of single bead peptide libraries was developed by certain of the present inventors to generate one-bead one-oligonucleotide libraries where each bead presents many copies of a single oligonucleotide sequence or species. See, e.g. Yang X, et al. Construction and selection of bead bound combinatorial oligonucleoside phosphorothioate and phosphorodithioate aptamer libraries designed for rapid PCR-based sequencing. *Nucleic Acids Research* 30 (2002) e123; Yang X, et al. Immunofluorescence assay and flow-cytometry selection of bead-bound aptamers. *Nucleic Acids Research* 31(10) (2003) e54; Gorenstein D G, et al. "Bead Bound Combinatorial Oligonucleoside Phosphorothioate and Phosphorodithioate Aptamer Libraries" (U.S. Pat. No. 7,338,762).

In one embodiment, copies of a single, chemically pure phosphorothioate oligonucleotide (S-ODN) are introduced onto each bead by the 'mix and separate' split synthesis method. Although oligonucleotides are relatively chemically stable, they are particularly susceptible to enzymatic degradation by nucleases. Controlled inclusion of modified residues such as thiophosphate (S-ODN) and dithiophosphate ($S_2$-ODN) residues is able to confer nuclease resistance and improve the binding properties of aptamers. See Gorenstein et al., U.S. Pat. No. 6,423,493.

In one embodiment, polystyrene beads with a non-cleavable hexaethyleneglycol linker attaching the first phosphoramidite are used such that the synthesized ODNs are still covalently attached to the beads after full base and phosphate ester deprotection. The aptamer oligonucleotide chains described herein will typically have sections that are non-random. For example, in a typical aptamer, at least the 5' and 3' termini constitute preselected sequences of PCR primers and may be generated by first nonrandom programmed stepwise addition to supports in one or more of the synthesis chambers. The 5' and 3' primer sequences may have functional roles in the ultimate aptamer. For example, the 5' and 3' sequences may be designed to contribute to a resulting stem-loop structure as will be later discussed.

The bead based process avoids the many rounds of solution enrichment and amplification of potential binding agents required by SELEX, and so can be accomplished much faster than SELEX, usually in one or two rounds. This is because each bead of the bead based library contains thousands of copies of the identical sequence and will therefore capture sufficient labeled target to be selectable in the first instance. With SELEX there will not be detectable numbers of copies of a given sequence for many rounds of amplification. Additionally, while the SELEX process is limited to binding agents (aptamers) consisting of nucleic acids that can be generated enzymatically, the bead-based process is not constrained by the type of nucleic acids (normal or chemically modified) used in the starting library.

Where identification of the target selected oligonucleotides is to be conducted by PCR, the only limitation on applicable chemical modifications is whether a chemically modified sequence can be read by the DNA polymerase used in PCR. The location of the modification is determined by comparing the selected sequence with the column program to determine where the modification must be. With the sequence and the modification site in hand, the identified X-aptamer can be synthesized. In contrast, in SELEX, the PCR product must be a faithful copy of the original sequence which is impossible for many modifications because the DNA polymerase will only copy the sequence using unmodified nucleotides—it is unable to build a faithful copy that includes the modifications for the further required iterative rounds.

For purposes of the present method using PCR to read the selected sequence, all possible types of DNA modifications that can be chemically synthesized can be used with this method so long as a nucleic acid polymerase can read the sequence. Examples of potential modifications include 5'-dyes, 5'-chemical linkers, and 5'-metal chelators. Certain of these may be useful for visualization of beads binding to tissue, for example.

Also suitable for use with PCR reading of the selected sequence are any nucleic acid polymerase readable sugar polymer types, such as for example arabinose-based polymers. If readable by PCR, where this method of determining the sequence is employed, modifications can be either in the backbone, the deoxyribose (and ribose) sugars, or the bases.

Figure 12:
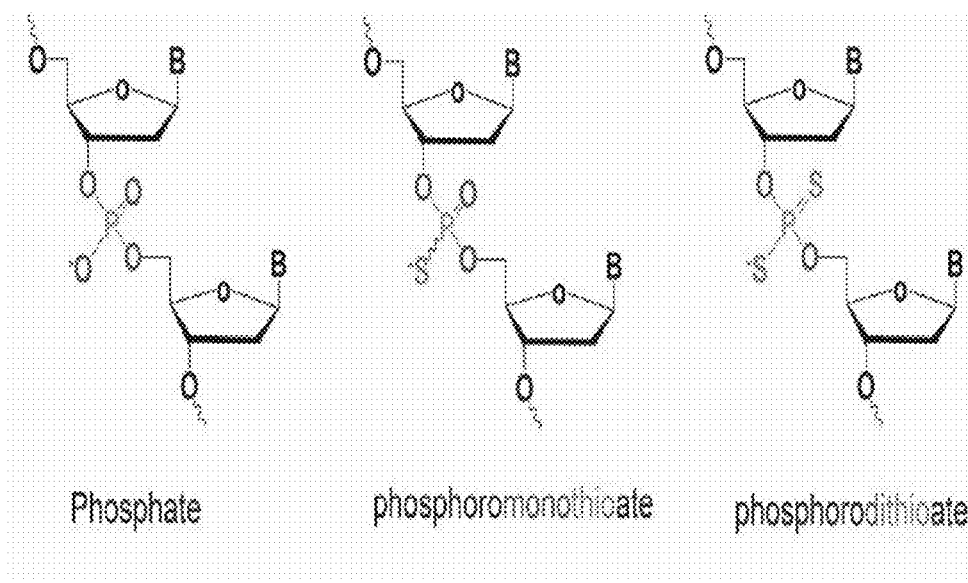
FIG. 12 depicts the structures of a normal phosphate compared with phosphomonothioate and phosphodithioate.

Non-limiting examples of backbone modifications include phosphate (normal), monothioate, dithioate, methyl phosphonate, alkyl phosphonate. FIG. 12 shows the structures of monothioate and dithioate phosphates compared with a normal phosphate. The thioates provide enhanced nuclease stability and can enhance aptamer binding affinity without sacrificing specificity. As can be seen, the phosphorodithioates are achiral at phosphorus. The thioates can be read in a sequence bearing them by PCR and, after identification of the thiolated bases by reference to the column protocol used to generate the library, thioates can be incorporated at selected positions during chemical synthesis after target binding. The dithioates are incompatible with conventional SELEX because they cannot be incorporated into synthesized stands by the polymerase.

Non-limiting examples of sugar modifications include (Deoxy)-Ribose-2'-fluoro, 2'-OMe, 2'-methyl, and 2'-deoxy-2'-fluoro-D-arabinose.

Non-limiting examples of base substitutes include 5-(3-aminoallyl)-deoxyuridyl, 5-(alkynyl)-deoxyuridyl, and 3-(2-Deoxy-b-D-ribofuranosyl)-1,3-diaza-2-oxophenothiazine. Many other modifications of base substitutes are possible so long as a nucleic acid polymerase can read the sequence that includes the modification. FIGS. 13A-D shows the structures of several exemplary base substitutes including: 5-(3-aminoallyl)-deoxyuridyl (FIG. 13A); 5-(3-aminoallyl leucyl)-deoxyuridyl (FIG. 13B); 5-(3-aminoallyl phenylalanyl)-deoxyuridyl (FIG. 13C); and 5'-Dimethoxytrityl-5-(pyren-1-yl-ethynyl)-2'-deoxyUridine, 3'-[(2-cyanoethyl)-(N,N-diisopropyl)]-phosphoramidite (FIG. 13D). The various potential base substitutions permit virtually unlimited chemical functionality including addition of positive charges, hydrophobic groups, amino acids, and small molecule drugs. After selection and identification, the base substitutions can be easily incorporated at selected positions, directly during synthesis or post-synthetically using amide coupling or click-chemistry. The present technology provides a means to include these modifications, which are incompatible with techniques such as SELEX that rely on amplification of faithful copies with each round of selection.

Figure 15:
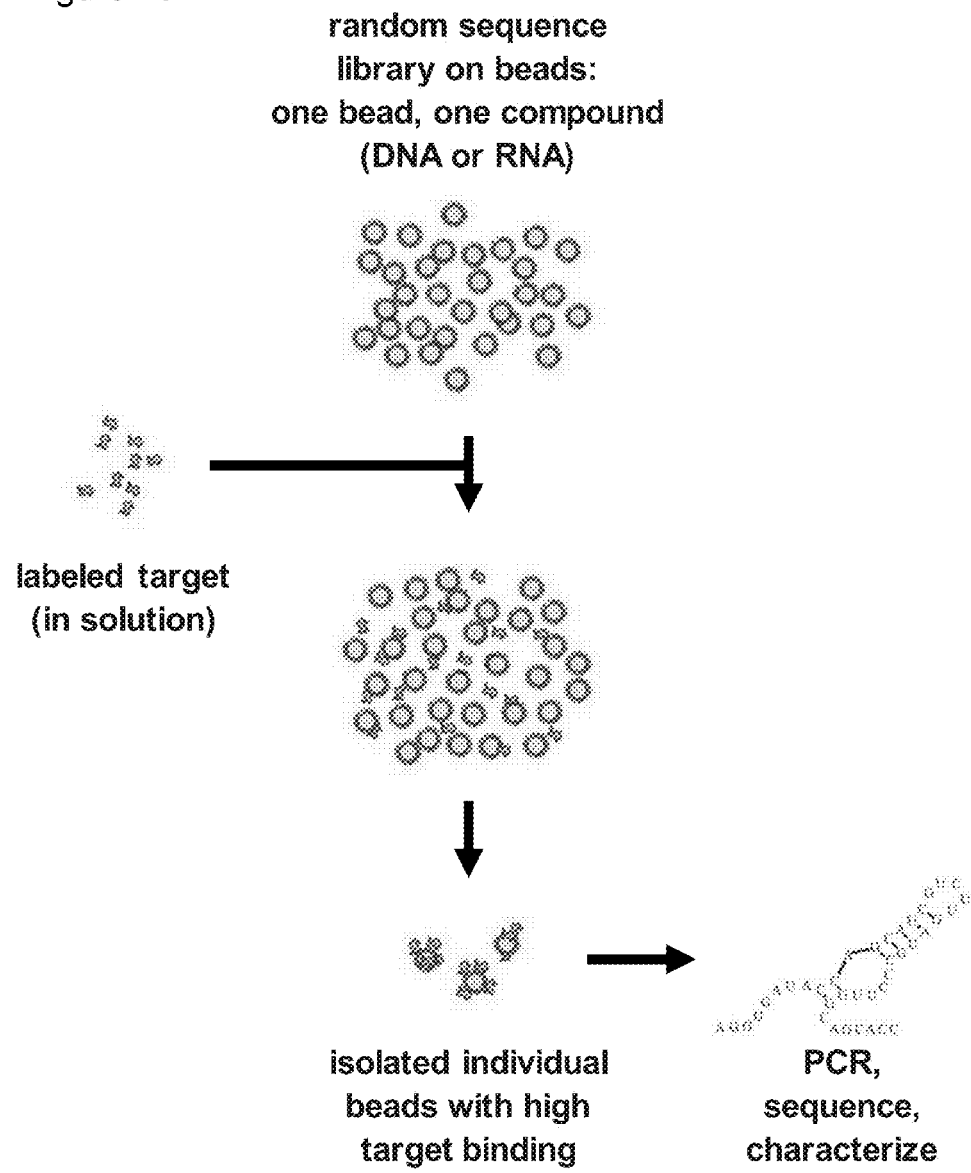
FIG. 15 is a cartoon of the general isolation method for target specific beads from a bead library.

In one exemplified embodiment of the present disclosure, high binding affinity partially monothioate DNA aptamers are first selected against a desired target. These aptamers can be selected by methods such as SELEX or from bead-based libraries as generally depicted in FIG. 15. It is noted in this context and for purposes of clarification, that SELEX can only be used to select partially monothioate aptamers as used as the starting material of EXAMPLE 1. For fully monothioate aptamers as starting materials, a bead-based process would be employed because SELEX cannot be used to prepare fully monothioate aptamers.

As shown on FIG. 15, in bead based library selection each bead is constructed to have many copies of the same unique sequence on its surface. After binding to labeled target, beads binding high amounts of the target are selected and isolated from the remaining majority of beads, which bind no or low amounts of the target. Bead selection can be achieved by any suitable method. For example, the target can be rendered fluorescent (by attachment of fluorescent dyes), and beads that bind large amounts of the target can be identified by their high fluorescence relative to other beads. Such beads can be isolated by manual recovery using a micropipettor, by automated fluorescence-activated sorting. The sequences on the selected beads are determined, most typically by PCR combined with sequencing and characterization of the sequence. Where X-groups have been added to the sequences during construction, the location of the X-groups is determined by consulting the program by which the nucleotides were added to the beads. This method has considerable advantages including very high selective enrichment, isolation in a single cycle, no PCR amplification bias and no chemistry limitations, except, in the case of sequence determination by PCR, that the nucleic acid polymerase be able to read the sequence on the bead.

Figure 14:
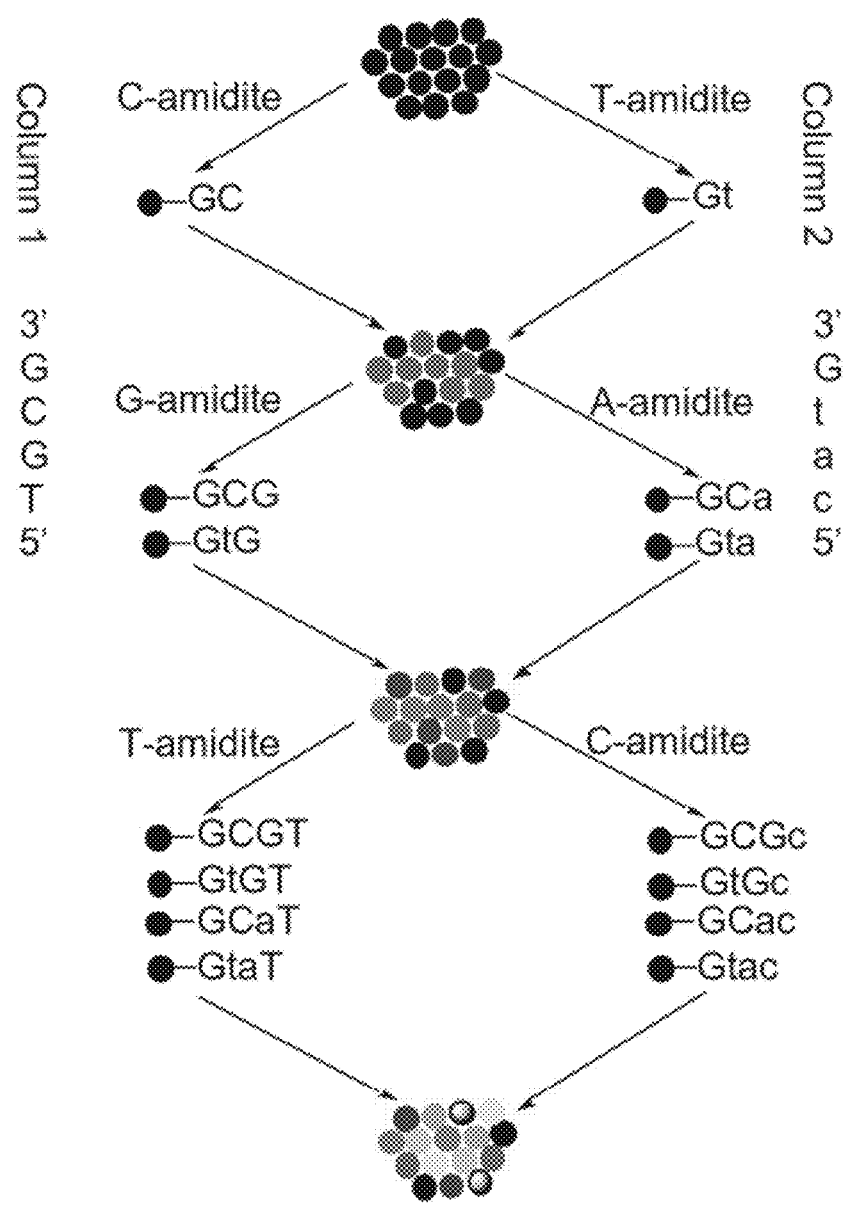
FIG. 14 is a cartoon depicting three split and pool steps for bead based library generation

FIG. 14 presents a simplified 2 column depiction of the output of the bead library synthesis process through three split and pool steps. In a preferred embodiment, the synthesis is undertaken in a fully automated DNA split pool synthesizer, which was developed by certain of the present inventors. Through this method, chemical modifications can be incorporated randomly into the library at any position, not just conventional dNTPs.

In the examples presented herein, pre-selected aptamers served as the lead sequences for the design of high-sequence-diversity XA although it is also possible to incorporate X groups into a random library from the beginning That is, it's not necessary to start with an existing aptamer sequence and then try to improve it by adding X groups at random positions.

One embodiment presented herein provides the first example of X-aptamers that are endowed with both nuclease resistance and expanded chemical functionalities, specifically drug-like molecules added to 5-positions of certain uridines on a completely monothiophosphate-backbone substituted oligonucleotide aptamer. By combining one-bead, one-sequence thioaptamer selection method with the incorporation of pseudo-randomly placed bases containing chemical linkers, additional X-ligands can be appended onto aptamers or thioaptamers to create a next-generation, X-aptamer library, and the best binding X-aptamers can be selected from this large pool of sequences.

In one embodiment disclosed herein, an exemplary reaction incorporates an X- moiety, 5-[N-(2-aminoethyl)-3-(E)-acrylamido]-2'-deoxyuridine, referred to herein as "amino-dU" to various positions in the XA library via Glen Research (22825 Davis Drive, Sterling, Va., 20164, US) Amino Modifier C2 dT phosphoramidite.

The structure of amino-dU is shown below:

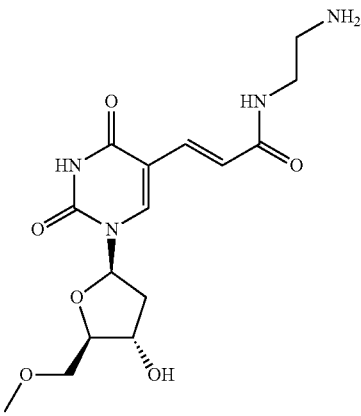 [SMILES: COC[C@H]1O[C@@H](n2cc(/C=C/C(=O)NCCN)c(=O)[nH]c2=O)C[C@@H]1O]

The structure of amino C2 dT is shown below:

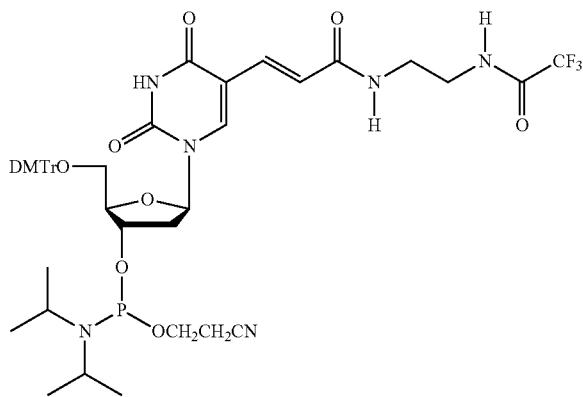

Four sequences were programmed for four different columns and designed for coding the positions of amino-dU. This library served as a basis from which additional X-aptamer libraries were made by conjugating through amide chemistries different carboxylated chemicals (ligands, drug-leads) onto the amino groups. As will be later described, this can also be achieved by using "click" chemistry of alkyne and small molecule azides. The amino-dU modification exemplified in Example 1 herein is just one of a large number of modified bases that can be used in such an approach. The bead-based selection and barcoding identification processes can accommodate any modified 5-X-dU phosphoramidite (even a large hydrophobic pyrenyl group). Due to the barcoding system, a T or X can be put into any position so long as the sequence is readable by PCR if PCR is to be used for sequence determination.

The X-groups may have been previously chosen by any of a number of methods, including without limitation, groups predicted to bind to the target molecule by in silico molecular modeling, groups identified by high-throughput chemical screens, and/or using SAR by NMR studies of small molecules libraries (Shuker et al. *Discovering High-Affinity Ligands for Proteins: SAR by NMR*. 274 Science (1996) 1531-1534).

In contrast, while some modified bases can be accommodated in the traditional SELEX methodology, many cannot because the modification itself must be incorporated into the ODN during PCR in order to be selected through SELEX. In contrast, in the processes disclosed herein, it is only required that the modified template can be read out by the polymerase. Multiple different modifications can be incorporated at either random or pre-specified positions within a single library. These capabilities dramatically expand the binding potential and functionalities of thioaptamers/X-aptamers.

The present disclosure provides a significant improvement to the generation of representational combinatorial libraries by automated synthesis in that the resulting X-aptamers feature both nuclease resistance and expanded chemical functionalities. The realized goal of the research leading to the present disclosure was to develop a new class of X-aptamers with enhanced binding affinity and specificity to a target protein. By introducing protein binding small drug molecules into the 5-position of dU residues at the random position of the aptamers and/or replacing one or more of the non-bridging phosphate oxygens with sulfurs, we are able to select an X-aptamer with 40 nM affinity to the exemplary CD44-HABD molecule through a non-iterative bead-based selection from large combinatorial libraries. Unlike the original aptamer concept, which mainly depends on the scaffold and sequence of the self-folding oligonucleotides, the X-aptamer has simultaneous interactions with target protein resulting from conjugated organic binding partners (or even amino-acid-like sidechains) as well as the X-aptamer oligonucleotide backbone. Such X-aptamers have applicability to the regulation of cancer related proteins, delivery of cancer-fighting drugs directly to cancer cells, and imaging and diagnostics among others.

The following examples are included for the sake of completeness of disclosure and to illustrate the methods of making the compositions and composites of the present invention as well as to present certain characteristics of the compositions. In no way are these examples intended to limit the scope or teaching of this disclosure.

EXAMPLE 1

Complete Monothioate Backbone Substituted Aptamer to CD44-HABD

As one example of starting material, in a previous report, certain of the present inventors described thioaptamers substituted with monothiophosphates on the 5' side of dA that bind to the hyaluronic acid binding domain of CD44 (CD44-HABD) ($K_D$=187-295 nM). Somasunderam A et al. *Biochemistry* 49 (2010) 9106-9112. The sequences of the original preselected aptamers are shown in FIG. 1A. In the preselection, 6 sequences were isolated of which TA1 and TA2 (in bold) differed by a single nucleotide. Based on the primary sequence of several of these thioaptamers and observed variations, a pseudo-random, one-bead-one-sequence bead library of aptamers was synthesized using an automated four-column, split-pool synthesizer as described in Englhardt U.S. Pat. No. 7,576,037. FIG. 1B shows the sequences programmed into each of Columns 1-4 (CL1-4) of the synthesizer. Of these, CL1 was programmed to have the addition sequence of TA1, without addition of any X-modifications. Each * in FIG. 1B represents a pool-split step. The first split occurs when beads are initially loaded into four columns, and the tenth pool occurs at completion of synthesis. Thus only nine of the ten total pool/split steps are indicated by an * in FIG. 1B.

The pseudo-random, one-bead-one-sequence library included ~$10^6$ ($4^{10}$) one-bead one-ODN each consisting of a 30 nucleotide combinatorial sequence (9 split/pool steps) flanked by two defined primer regions at the 5' and 3' ends. By "pseudo-random" it is meant that the sequences programmed on the columns are derived in part from pre-selected aptamer sequences. The central region contained ten parts, each of which could have 1 of 4 possible sequences, determined by the path each bead takes during the split and pool method. The 3' ends of the sequences were covalently linked by a non-cleavable hexaethyleneglycol linker to a 65-μm polystyrene bead (ChemGenes).

The unique sequence on a given bead may contain zero to 12 X-positions, but three or four Xs is most likely. In order to select highly nuclease-resistant X-aptamers, the library was prepared with a fully monothiophosphate (permonothioated) backbone. To our knowledge, this is the first example of the selection of an X-aptamer with complete monothioate backbone. It is noted that complete monothioate backbone aptamers are unable to be developed by the SELEX process, which requires iterative selection to identify a target binding aptamer. Because no more than three different alpha-S-dNTPs can be used in the enzymatic amplification steps using Taq polymerization, the required amplification iterations of SELEX cannot select a completely monothioated aptamer.

This original pseudo-random, one-bead-one-sequence bead library served as the base library from which a variety of additional X-aptamer libraries were derived by conjugation with NHS-ester forms of drug-like molecules. To select small molecule ligands as binding affinity enhancers that could be attached to the X-aptamer base library, in silico screening was carried out using AMBER (Case et al. AMBER9 (2006) UCSF) and DOCK6.4 (Lang et al. RNA 15 (2009) 1219-1230). Specifics of the materials and synthesis are as follows:

Materials. The dA, dG, dC and dT cyanoethylphosphoramidites, and the Beaucage reagent (3H-1,2-benzodithiol-3-one 1,1-dioxide) were purchased from Glen Research. The Taq polymerase kits were from Applied Biosystems. The TOPO TA Cloning kit was obtained from Invitrogen. Polystyrene beads (60-70 μm) with non-cleavable hexaethyleneglycol linkers with a loading of 36 μmol/g were purchased from ChemGenes Corp. (Ashland, Mass.). The oligodeoxynucleotides (ODNs) and monothioated S-ODNs used in the study were synthesized on a 1 μmol scale in an Expedite 8909 System (Applied Biosystems) DNA synthesizer. NHS-PEG$_{12}$-biotin was purchased from Pierce. N-acetyl-2,3-dehydro-2-deoxyneuraminic acid (ADDA) was purchased from Sigma-Aldrich.

Synthesis of S-ODN library. Standard phosphoramidite chemistry was used for the synthesis of the S-ODN library. The library was prepared using an automated four-column, split-pool synthesizer on a 1 μmol/column scale on polystyrene beads. After first synthesizing the 3'-primers, the pseudo-random sequences were programmed, one section at a time, on the four columns of the synthesizer to create the combinatorial S-ODN library as shown in FIG. 1B. In the FIG. 1B, X=5-(aminoethyl-3-acrylimido)-deoxyuridine created by incorporation of "Amino Modifier C2 dT" (Glen Research), asterisks represent the occurring of a split and pool synthesis step, and the primer region is shown in bold.

Subsequent addition of the 5'-primer completed the 73mer ODNs. A 'split and pool' occurred at each position indicated by an asterisk in order to synthesize the combinatorial region for the S-ODN. The example sequence (EX) in FIG. 1B is one example of an ODN that would result from a bead that followed the column path (from 3' to 5') 3-4-2-4-1-3-2-4-2-1, depicted as underlined parts, during the split-pool method. The step-wise coupling yields were approximately 99% as determined by the dimethoxytrityl cation assay. Sulfurization chemistry utilized the Beaucage reagent. The S-ODN combinatorial libraries on non-cleavable linker beads were deprotected with concentrated ammonium hydroxide at 37° C. for 21 h. and then washed with doubly distilled water.

Expression and Purification of CD44-HABD. DNA encoding CD44-HABD (amino acid residues 20-178) was synthesized and cloned into expression vector pET19b between the NdeI and BamHI sites. Protein expression, refolding and purification followed published procedures (Banerji, S.; et al. *Protein Expression and Purification* 14 (1998) 371-381). The purity of CD44-HABD was analyzed by gel electrophoresis (SDS-PAGE and native PAGE). The concentration of CD44-HABD was determined by UV-Vis Spectrophotometry (276 nm, ε=12.95 mM$^{-1}$ cm$^{-1}$) and BCA assay (Pierce).

Labeling CD44-HABD protein with biotin. To 130 μL of CD44-HABD (40.5 μM) in PBS was added 1.2 μL of NHS-PEG$_{12}$-biotin (125 mM in DMF). The reaction was incubated on ice for two hours. Biotin labeled protein was purified from non-reacted biotin reagent using Zeba desalt spin columns (Thermo Scientific). The labeled protein was stored at 4° C.

Conjugation of ADDA to XA bead library. To 1 μL of a 1 molar ADDA solution in DMSO, 5 μL of a freshly prepared ethyldimethylaminopropyl carbodiimide (EDAC) solution (1 molar in H$_2$O) and 5 μL of an N-hydroxysuccinimide (NHS) solution (1 molar in DMSO) were added. The reaction was kept at room temperature for one hour. To couple ADDA to the original X-aptamer bead library, 10% of the original XA library was added, and the resulting mixture was gently shaken overnight. Beads were washed to remove unused reagents, and the conjugation was confirmed by a ninhydrin test.

Selection of the ADDA-modified X-aptamer library against CD44-HABD. The screen began with the ADDA X-aptamer library incubated in PBS (pH 7.4) containing Tween 20 (0.1%, v/v) and bovine serum albumin (BSA, 0.1%) for one hour, with shaking, to block non-specific protein binding. The library was then washed with PBS (pH 7.4). A negative selection was carried out first by incubating the washed X-aptamer beads with streptavidin-coated Dyna beads (Invitrogen) for two hours at room temperature. The slurry of the beads mixture was allowed to slowly pass in solution near a magnet to remove the Dyna beads and any X-aptamer beads which have the Dyna beads bound non-specifically on their surface. The rest of the X-aptamer beads were then suspended in a dilute solution of biotinylated CD44-HABD (0.01 nM in PBS, pH 7.4) at room temperature overnight. After washing with PBS containing 0.1% Tween-20 and BSA, PBS containing 0.1% Tween-20, and PBS, the library was incubated with streptavidin-coated Dyna beads for two hours at room temperature. The beads were washed thoroughly with PBS containing 0.1% Tween-20 and BSA, PBS containing 0.1% Tween-20, and PBS. The positive X-aptamer beads, which had CD44-HABD bound tightly, were isolated from the incubation by passing the beads in solution near a magnet. The positive beads were transferred onto a glass microscope slide and selected manually by pipette. To remove bound proteins, each positive bead was incubated in 8 molar guanidine hydrochloride for one hour then rinsed ten times with water.

One-bead one-PCR amplification and sequencing of PCR products. The washed beads were directly used for the 'one-bead one-PCR' amplification process using the 5' end and the 3' end primers shown below:

```
5' PRIMER:
5'-GAGATTCATCACGCGCATAGTC-3'      SEQ. ID. 25

3' PRIMER:
5'-CGACTATGCGATGATGTCTTC-3'       SEQ. ID. 26
```

A selected single bead was mixed with the following PCR components: 6 μL of 25 mM MgCl$_2$, 0.5 μL of Taq polymerase (5 U/μL), 1 μL of 8 mM dNTP, 10 μL of PCR buffer, and 1 μL of 40 mM primers. The PCR was run on a GeneAmp PCR system 2400 (Perkin Elmer). The PCR mixtures were thermal cycled using the following scheme for amplification: 94° C. for 5 min (1 cycle); 94° C. for 1 min, 40° C. for 2 min and 72° C. for 1 min 10 sec (35 cycles); 72° C. for 10 min (1 cycle). The PCR product was inserted into pCR2.1 TOPO TA vector (Invitrogen) and sequenced. PCR amplification converts the original X modifications to Ts. X positions were determined by reference to the original library design (FIG. 1B), using the adjacent bases as "barcoding". FIG. 1C lists the XA sequences obtained (XA1-13, SEQ ID NOs 12-24). Typically the derived XA will be resynthesized off the non-cleavable linker beads for verification and then conjugation with desired ligands.

Conjugation of ADDA to XAs in solution. To 1 μL of a 1 molar ADDA solution in DMSO, 5 μL of a freshly prepared EDAC solution (1 molar in H$_2$O) and 5 μL of an N-hydroxysuccinimide (NHS) solution (1 molar in DMSO) were added. The reaction was kept at room temperature for one hour. To couple ADDA to XAs in solution (not on beads), XAs (0.05 μmol) were dissolved in 100 μL of sodium bicarbonate buffer (0.1 molar, pH 8.5). ADDA-NHS ester solution was added to the solution of XAs. The mixture was first vortexed and then shaken at room temperature for four hours. The ADDA-modified XAs were purified by reverse phase HPLC on a Hamilton PRP-1 column. Buffer A: 100 mM triethylammonium acetate in H$_2$O (pH 7.5); buffer B: acetonitrile. Gradient: 0-40% B, 0-60 min; 40-100% B, 60-70 min; 100-0% B, 70-75 min. Flow rate was 2 mL/min. The fractions of ADDA-modified XAs were combined, lyophilized and analyzed by 15% PAGE.

$^1$H,$^{15}$N-HSQC NMR Data for CD44-HABD. $^1$H,$^{15}$N-HSQC data were collected on an 800 MHz Varian UnityPlus spectrometer (Rice University) equipped with a cryogenic probe using 32 transients per fid, sweep widths of 3.2 kHz and 11.2 kHz for f1 ($^{15}$N) and f2 ($^1$H), respectively, and 128 and 1912 complex data points for f1 and f2, respectively. Data were processed using VNMRJ (Varian, Inc.) or Felix (Felix, Inc.) software. The proton dimension was referenced to TSP and nitrogen shifts were referenced indirectly. CD44-HABD was prepared in the NMR buffer (20 mM Tris, 50 mM NaCl, 10% (v/v) D$_2$O, pH 6.7). ADDA was dissolved in DMSO (1.0 M) as stock solution. CD44-HABD (70 μM) with ADDA (7 mM) was prepared in the same buffer (20 mM Tris, 50 mM NaCl, 1.25 mM ADDA, 0.7% (v/v) DMSO, 5% (v/v) D$_2$O, pH 6.7).

ADDA binding to CD44-HABD. CD44-HABD was prepared in the NMR buffer (20 mM Tris, 50 mM NaCl, 5% (v/v) D$_2$O, pH 6.7). ADDA was dissolved in DMSO (1.4 M) as stock solution. The ADDA sample for NMR was prepared in the same buffer (20 mM Tris, 50 mM NaCl, 1.25 mM ADDA, 0.1% (v/v) DMSO, 5% (v/v) D$_2$O, pH 6.7). CD44-HABD (27 µM) with various concentration of ADDA (14 µM, 25 µM, 50 µM, 250 µM and 1250 µM) was also prepared in the same buffer. The $^1$H-NMR spectra of CD44-HABD only, ADDA only and CD44-HABD in presence of ADDA were obtained.

Figure 2B:
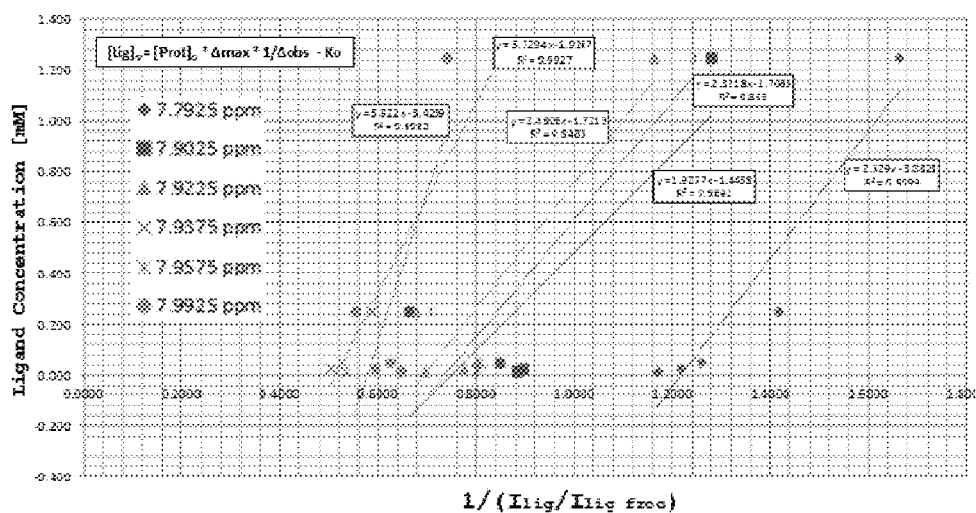
FIG. 2B shows the intensity changes of peaks that were selected in order to obtain a statistical value of the dissociation constant of the ligand ADDA.

The equilibrium dissociation constant of ADDA to CD44-HABD was determined by $^1$H-NMR. FIG. 2A shows a set of spectra measured on changing the concentration of the ADDA ligand, where $I_{lig}/I_{lig-free}$ represent the ratio between the intensity of the signal of the protein CD44-HABD with and without the ligand. The $^1$H-NMR spectrum of the ligand alone showed no signal in the region of interest that could have interfered with the signal intensity ratios. Several peaks were selected (7.7925, 7.9025, 7.9225, 7.9375, 7.9575 and 7.9925 ppm) in order to obtain a statistical value of the dissociation constant of the ligand ADDA, $K_D$=2.22±0.82 mM, as shown in FIG. 2B and summarized in the following Table 1:

TABLE 1

DISSOCIATION CONSTANT OF THE LIGAND ADDA

| peak (ppm) | 7.7925 | 7.9025 | 7.9225 | 7.9375 | 7.9575 | 7.9925 | Average $K_D$ |
|---|---|---|---|---|---|---|---|
| $K_D$ [mM] | 3.0823 | 1.4438 | 1.7213 | 1.9167 | 1.7083 | 3.4259 | 2.22 ± 0.82 |

Filter binding assay. The equilibrium binding constants of selected XAs for CD44-HABD were determined by a filter binding assay. The biotinylated XAs (1 nM) were incubated with varying concentrations of CD44-HABD in 50 µL of 20 mM Tris, pH 8.0, 150 mM NaCl for 40 min at room temperature and then transferred to a 96-well dot-blot apparatus and filtered under vacuum onto nitrocellulose membranes, which retain the CD44-HABD along with any bound XAs. The amount of biotinylated XA retained at each spot was determined by chemiluminescent detection using the Chemiluminescent Nucleic Acid Detection Module (Thermo Scientific) following the manufacturer's instructions. The chemiluminescent signals were collected on a Chemimager (Alpha Innotech). Image analysis and quantification of spot intensities were performed using ImageJ (version 1.42q). Binding analysis was based on the spot intensities on the nitrocellulose membranes with subtraction of background spot intensity due to the buffer effect from all the data points. Saturation binding curves were generated by using Graph-Pad Prism with curve fits assuming a single binding site. The equilibrium dissociation constants, $K_D$, were derived from these curves and are listed in Table 2. The NH$_2$ XA column lists $K_D$s for XAs where X=amino-dU. The ADDA XA column lists $K_D$s for XAs where X=ADDA-dU.

TABLE 2

EQUILIBRIUM DISSOCIATION CONSTANTS OF SELECTED PERMONOTHIOATED XAS TOWARD CD44-HABD

| | $K_D$ (nM) | |
|---|---|---|
| Name | NH$_2$ XA | ADDA XA |
| XA1 | 62.9 ± 10.3 | 108.7 ± 15.4 |
| XA2 | 55.5 ± 13.4 | 78.3 ± 18.1 |

TABLE 2-continued

EQUILIBRIUM DISSOCIATION CONSTANTS OF SELECTED PERMONOTHIOATED XAS TOWARD CD44-HABD

| | $K_D$ (nM) | |
|---|---|---|
| Name | NH$_2$ XA | ADDA XA |
| XA3 | 110.9 ± 18.5 | 139.6 ± 16.8 |
| XA4 | 137.4 ± 37.4 | 102.7 ± 16.8 |
| XA5 | 137.4 ± 37.4 | 124.8 ± 38.4 |
| XA6 | 213.9 ± 31.6 | 150.0 ± 25.7 |
| XA7 | 305.8 ± 69.3 | 116.3 ± 20.7 |
| XA8 | 463.2 ± 82.4 | 274.0 ± 54.3 |
| XA9 | 476.9 ± 89.5 | 555.5 ± 108.1 |
| XA10 | 449.9 ± 180.3 | N.A. |
| XA11 | 845.6 ± 151.4 | 1086.0 ± 390.5 |
| XA12 | 962.6 ± 182.7 | 878.7 ± 134.9 |
| XA13 | 1377.0 ± 237.0 | 312.5 ± 68.53 |

Figure 3A:
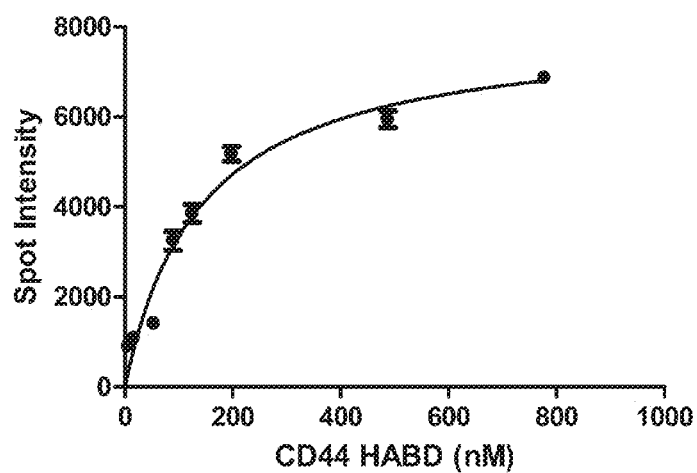
FIGS. 3A and B respectively illustrate the binding curves of ADDA XA3 (SEQ ID 14, where X=ADDA-modified dU) and ADDA XA7 (SEQ ID 18, where X=ADDA-modified dU).
Figure 3B:
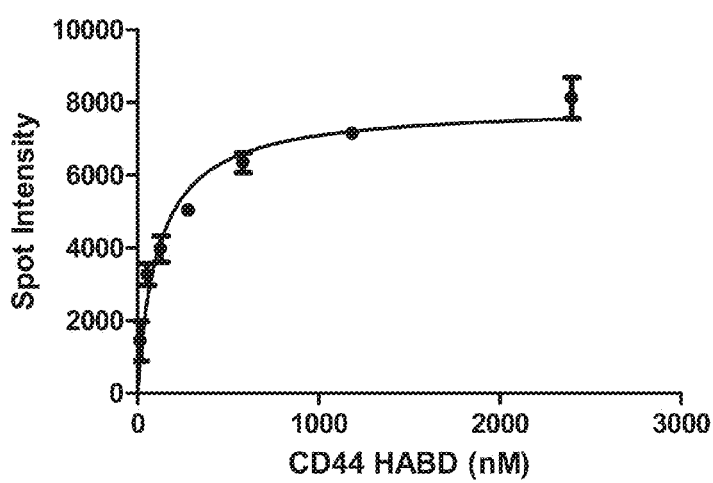

The binding curves of ADDA XA3 and ADDA XA7 are shown in FIG. 3A and FIG. 3B, respectively. MFold-predicted secondary structures indicated that all selected XA sequences can form hairpin loop structures with the random region forming the loop and the primer regions making up the stem regions (FIGS. 4A and B). Primer regions are in black while random regions are circled. The sequence of the 5' primer is SEQ. ID. 25, while the sequence of the 3' primer is SEQ. ID. 26. Proposed binding motifs are encircled with a solid line. The positions where ADDA was coupled are also shown. From these binding motifs based on the predicted secondary structures, several smaller constructs were made of various stem-loop regions of these selected X-aptamers (EXAMPLE 2).

Molecular Dynamics Simulation protocol. The initial structure (human CD44-HABD, 1POZ.pdb) was neutralized by adding Na$^+$ counter ions using an algorithm of xLeap (AMBER9 suite of programs). The latter structure was then surrounded by a 10 Å layer of TIP3P model water molecules in an orthorhombic box of approximately 60×72×90 Å containing a total of 28386 atoms. The system was minimized by 1000 steps steepest descent method then 4000 steps of conjugate gradient. The solvated system was then equilibrated as follows i) 40 ps MD simulation to gradually heat the system from 0 to 300K keeping all molecules restrained by 25 kcal mol$^{-1}$ Å$^{-2}$ under NVT conditions, ii) 20 ps MD simulation at 300K with all molecules restrained by 25 kcal mol$^{-1}$ Å$^{-2}$ under NVT conditions, iii) the system was subsequently equilibrated in 7 MD simulation rounds over 1180 ps where the positional restraints were gradually relaxed under NPT conditions at 300K and finally a structure production run of 10 ns MD simulation at 300K under NPT conditions was performed. The long-range electrostatics were accounted for using the particle-mesh Ewald summation method, as implemented in the PMEMD module of AMBER9, and the force field ff99SB was applied. The SHAKE algorithm was used to constrain covalent bonds to hydrogen atoms allowing a time step of 2 fs. A cutoff of 9 Å was chosen for the non-bonded van der Waals interactions. During the heating protocol at NVT conditions, the Berendsen temperature coupling algorithm was used with a coupling constant of 2.0 ps. During the equilibration and production of the simulation, the Langevin dynamics were used with a collision frequency of 1.0 ps$^{-1}$.

This simulation allowed the identification of 4 representative structures using the cluster analysis algorithm on ptraj software (AMBER9 suite of programs). A second 10 ns MD simulation was performed including the hyaluronic acid ligand bound into the HABD this time. The same MD protocol was used as described before but applying the ff99SB+GLYCAM06 force field because of the nature of the hyaluronic acid ligand. Therefore, a second set of 4 representative structures were found using the cluster analysis algorithm on ptraj software (AMBER9 suite of programs). These 8 representative structures plus the original 1POZ.pdb structure were used as possible binding pockets for a virtual screening of small molecules.

Virtual Screening protocol. A group of 2553 possible ligands with modifiable groups allowing attachment of the ligand to the X-aptamer ODN scaffold were selected from ChemBridge database and 245 ligands from Sigma-Aldrich. Each ligand followed a 0.5 ns MD simulation on implicit water using the Generalized Born method at 300K in order to find and select an ensemble of possible rotamers. The rotamers were chosen using the following protocol: i) 20 ps to gradually heat the system from 0 to 300K, ii) 460 ps of production run at 300K and iii) 20 ps to gradually cool down the system from 300 to 0K. A total of seven rotamers per ligand were initially selected: the first rotamer was the initial structure of stage i) which is the original structure downloaded from the database, five more rotamers were found using the cluster analysis algorithm on ptraj software (AMBER9 suite of programs) from stage ii) and the final rotamer was selected at the end of stage iii). All rotamers were minimized with the Generalized Born method. Only rotamers >2.0 rmsd from the original structure (first rotamer) were considered.

Figure 7:
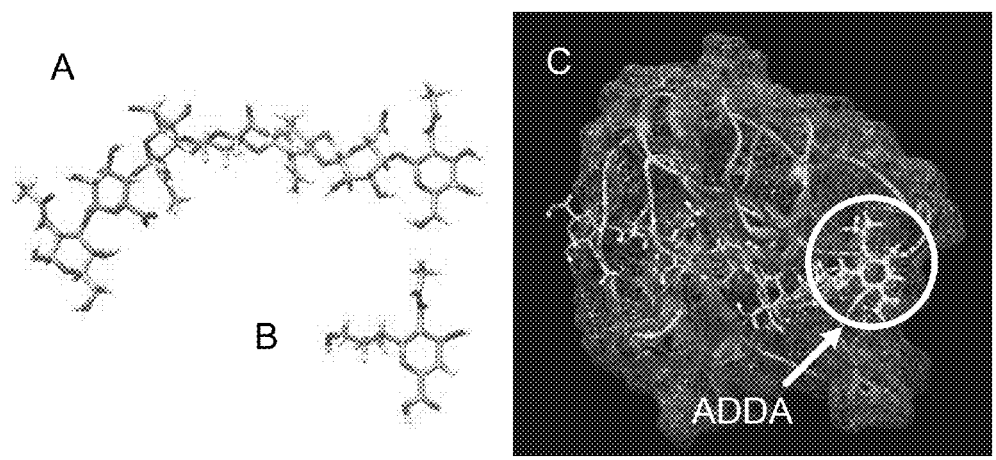
FIG. 7A shows the structure of a 7-mer hyaluronic acid (HA)
FIG. 7B shows structure of the ADDA ligand.
FIG. 7C shows a docking overlay of HA (bond representation) with ADDA ligand (circled) on the CD44-HABD.

After rotamer selection a semi-empirical quantum calculation (AM1-BCC method, AMBER9 suite of programs) was performed for each rotamer, and an average charge was calculated and used for all rotamers of the same ligand. The initial rotamer structures and their charges are critical components during the virtual screening process in order to get good lead compounds. Using DOCK6.4 software on the 9 representative protein structures with the 2798 small molecules, the ADDA ligand (N-acetyl-2,3-dehydro-2-deoxyneuraminic acid, PubChem: CID 65309) was selected as lead compound. In one example of the results of a similar process for ligand selection, FIG. 7A depicts the structure of a 7-mer hyaluronic acid (HA) built by xLeap (AMBER9 suite of programs), FIG. 7B depicts the structure of the ADDA ligand selected by the virtual screening protocol and FIG. 7C shows a docking overlay of HA (bond representation) with ADDA ligand (circled) on the CD44-HABD.

EXAMPLE 2

Second Generation X-Aptamers

Figure 4B:
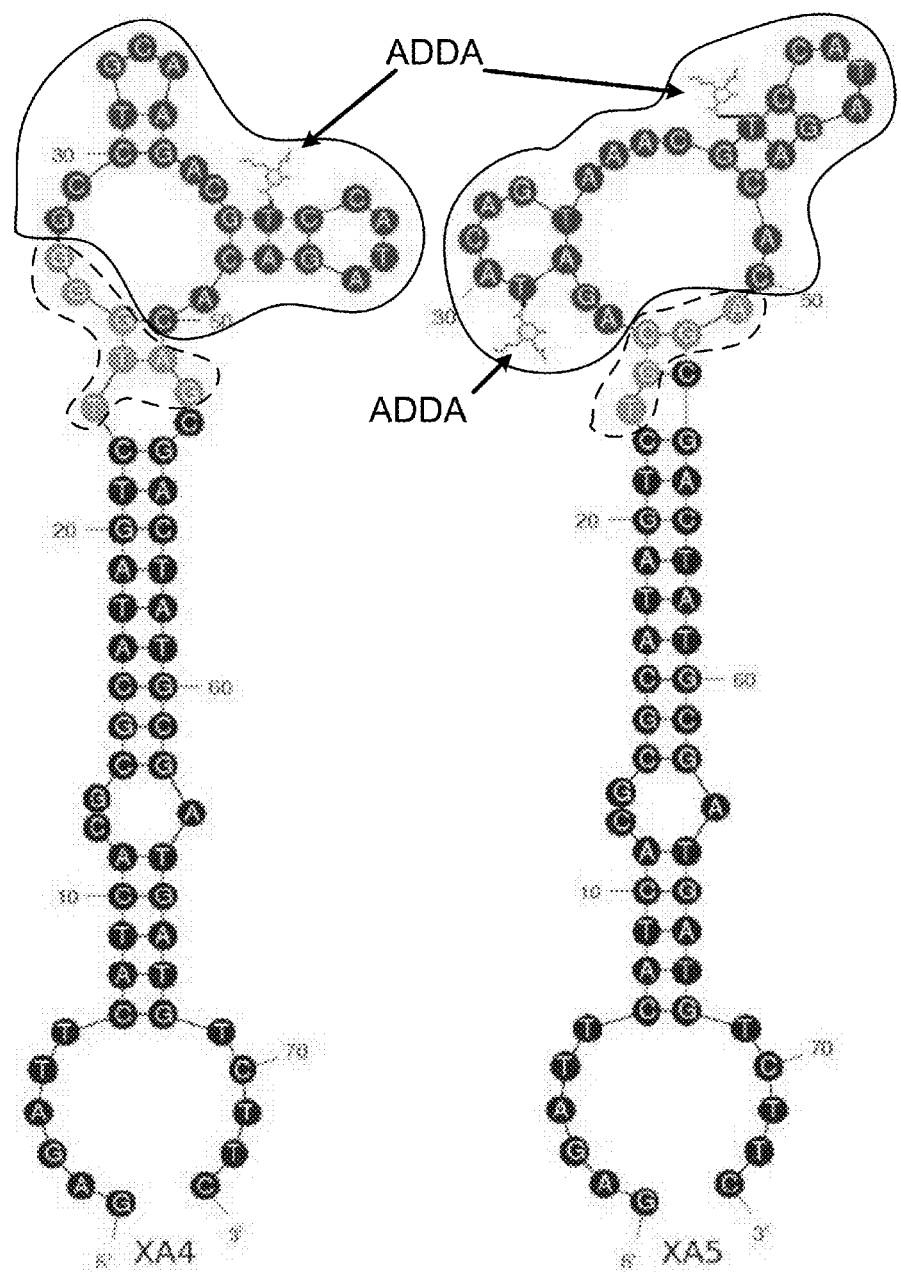
Figure 4C:
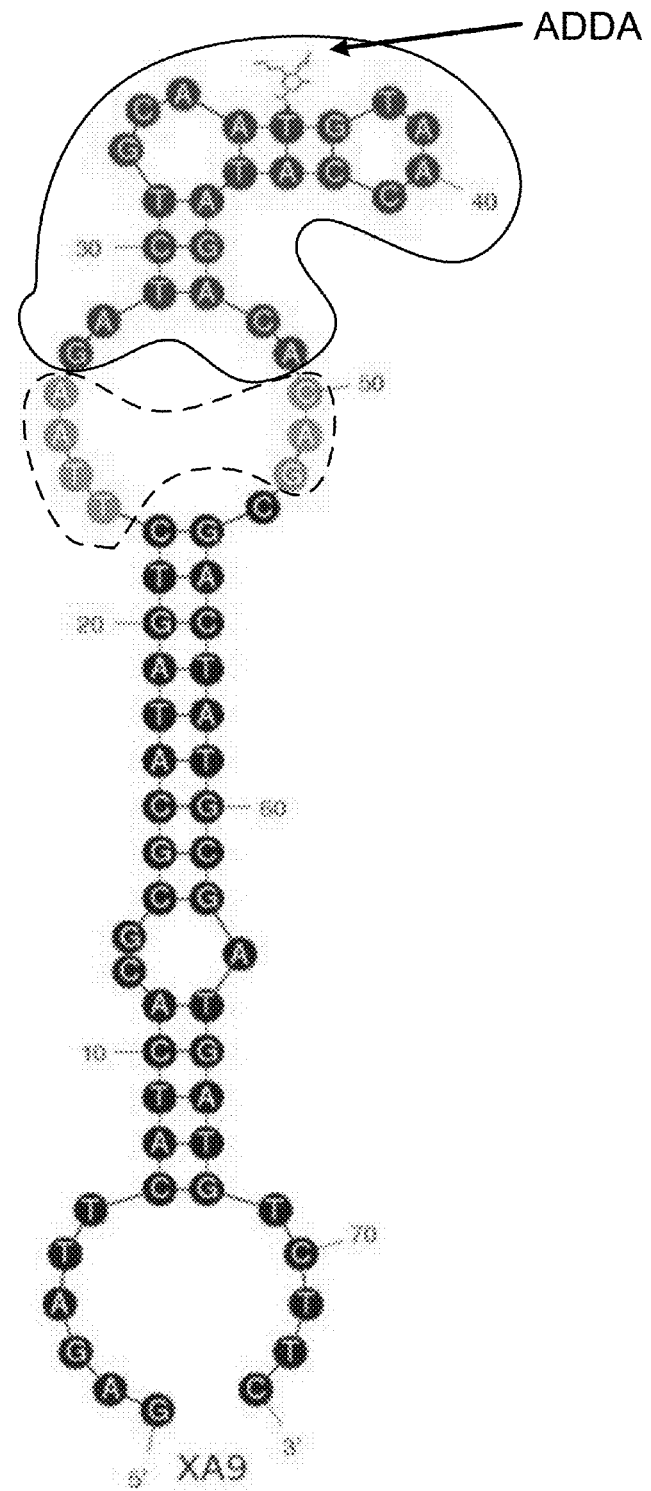

Secondary structure predictions performed using MFold (Zuker, M. *Nucleic Acids Research* 31 (2003) 3406-3415) suggested that all selected XA sequences can form hairpin loop structures in which the random regions form loops and the primers form stem regions as shown in FIGS. 4A-C. Based on these predicted structures, several binding motifs and smaller constructs of various stem-loop regions were identified. The sequences of these truncated XA-sequences are shown below in Table 3. Such truncation allows elimination of excessive X moieties if desired while keeping the ligand binding domain.

TABLE 3

SEQUENCES OF TRUNCATED X-APTAMERS

| Motif | Motif Sequence | SEQ ID |
|---|---|---|
| CL.1 | 5'PRIMERCCAAGGCCTGCAAGGGAACCAAG GACACAG3'PRIMER | 7 |
| 1 (XA2) | 5'-AAGGGAACCAAGGACACTAC-3' | 27 |
| 2 (XA1) | 5'-CXGXTAGGGAACCAAGACGA-3' | 28 |
| 3 (XA4) | 5'-GCCTGCAAGACGXCCATAGACAC-3' | 29 |
| 4 (XA9) | 5'-GATCTGCAAXGTAACCATAGACA-3' | 30 |
| 5 (XA5) | 5'-AGAXACAGTAAACGXCCATAGACAC-3' | 31 |

Figure 5A:
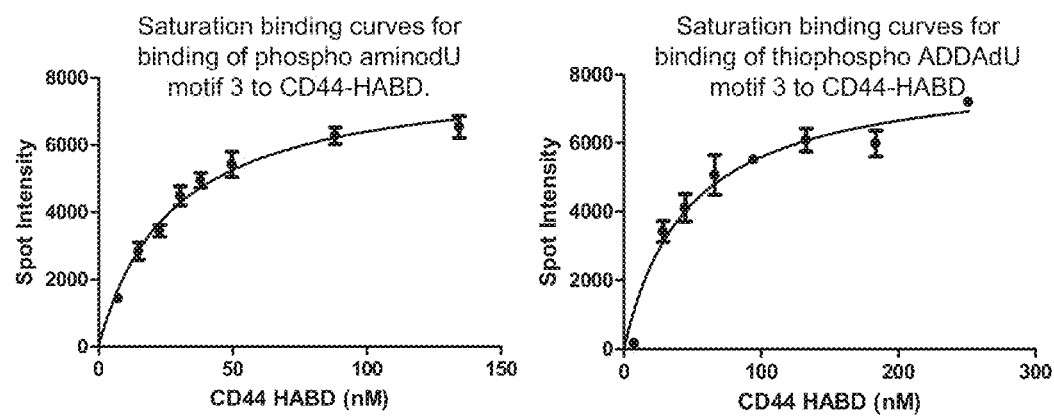
FIGS. 5A-C respectively represent the binding curves of truncated Motifs 3, 4 and 5.
Figure 5B:
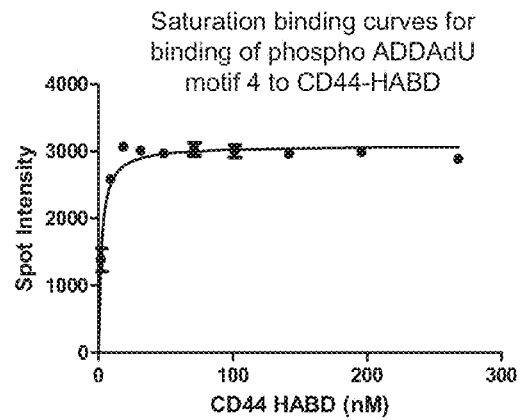
Figure 5C:
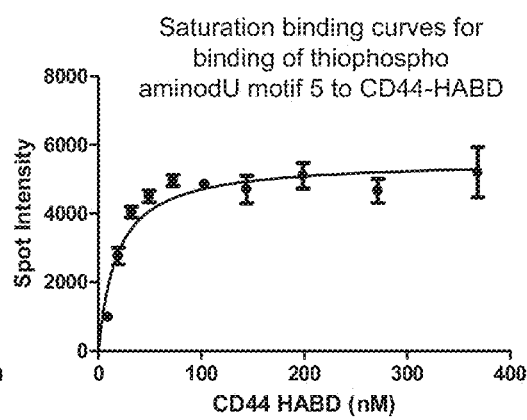

Alternating underlined bold letters correspond to the split-pool sequence sections in FIG. 1B for these aligned sequences. Following each motif number in column 1 above is the name of the parent aptamer of FIG. 1C from which the truncation was derived The equilibrium binding constants of the small constructs were determined by the filter binding assay. The binding curves of exemplary motif 3, motif 4 and motif 5 are shown in FIGS. 5A-C respectively. The derived equilibrium binding constants of the above small XA constructs are shown below in Table 4.

TABLE 4

EQUILIBRIUM BINDING CONSTANTS OF THE SMALL XA CONSTRUCTS OF TABLE 3

| | Dissociation constant (nM) | | | |
|---|---|---|---|---|
| Full-length parent sequence Cl.1, partially monothioated | 191 ± 25 | | | |
| Full-length parent sequence CL.1 permonothioated | 230 ± 47 | | | |

| | Phospho X-aptamers | | Thiophospho X-aptamers | |
|---|---|---|---|---|
| Motif | X = NH$_2$-dU | X = ADDA-dU | X = NH$_2$-dU | X = ADDA-dU |
| 1 | 10.3 ± 1.3 | | 15.0 ± 2.0 | |
| 2 | 43.1 ± 9.5 | 2.0 ± 0.6 | 48.0 ± 18.0 | 15.5 ± 3.2 |
| 3 | 27.6 ± 8.5 | 19.5 ± 3.2 | 81.2 ± 30.9 | 64.8 ± 13.7 |
| 4 | 6.8 ± 1.8 | 2.1 ± 0.2 | 35.4 ± 7.4 | 13.6 ± 3.0 |
| 5 | 13.8 ± 4.1 | 3.9 ± 1.0 | 18.0 ± 3.7 | 10.1 ± 2.6 |

ADDA-dU is the ADDA adduct with 5-(aminoethyl-3-acrylimido)-deoxyuridine.
Motif 1, which contains no X, was included to compare the phosphoaptamer and the thioaptamer forms.

Remarkably, coupling ADDA with smaller stem-loop constructs from the best X-aptamer sequences, motifs 2 and 4 (ADDA adduct) have ~2 nM affinity to CD44-HABD, which is an increase in binding affinity of ~115-fold between the full-length permonothioated parent sequence and the final ADDA-conjugated XA (phosphoform). Moreover, the ADDA-conjugated permonothioated motif 5 has ~10 nM affinity, which is an increase of ~23-fold compared to the permonothioated parent sequence. In every case in Table 4, the ADDA-conjugated XA showed increased affinity compared to the unconjugated XA. In the best case, ADDA conjugation increased affinity ~22-fold. ADDA is a weaker binder (~2 mM) to CD44-HABD. By conjugation to an aptamer, the binding affinity of ADDA modified XAs has improved the affinity 1 million fold (from 2 mM to 2 nM).

By introducing a protein binding small drug molecule, ADDA, into the 5-position of dU residues at random positions of the aptamers and/or replacing one of the non-bridging phosphate oxygen atoms with sulfur atoms, we are able to select an X-aptamer with <10 nM affinity to CD44-HABD through a non-iterative bead-based selection from large combinatorial libraries of X-aptamers. The present bead-based method is compatible with both monothiophosphate- and dithiophosphate-modified thioaptamers, and even complete monothiophosphate modification of the backbone, as reported here, which is not possible with traditional SELEX methods. In addition, the present method allows a given base, such as dT, to be replaced with a modified version of that base, such as amino-dU or ADDA-dU, in only a subset of positions, while the remaining dT positions remain unmodified. This is not possible with SELEX, which can only incorporate certain modified bases, and only by total replacement of the natural base with the modified version. Furthermore, the present method requires only one or two rounds of aptamer selection, in contrast to the 10-15 rounds typical in traditional SELEX.

As expected, the effect of ADDA as a binding affinity enhancer is location-dependent within the aptamer. The process of finding the optimal position of the ligand was part of the X-aptamer selection since ADDA was attached to the aptamers at various positions. By simultaneously selecting the optimal sequence of the aptamer scaffold and the orientation and position of the small drug presented by the optimal scaffold, enhanced affinities were achieved. The incorporation of ADDA not only expands the XA's chemical diversity but also the surface area of binding, thus the XA can also offer enhanced specificity.

While the present example describes conjugation with one specific drug at a time, multiple drug hits can be randomly attached as well, to provide enhanced combinations of binding moieties. More than one ligand can be attached by pausing the DNA synthesis for the addition of a ligand and then continuing the DNA synthesis and coupling reactions. By using two or more chemical linkers in one root library, multiple drugs can be selectively incorporated. The present methodology can be applied to most target proteins with a variety of small molecules to create highly chemically modified X-aptamers that have the combined characteristics of drug molecules, proteins and nucleic acids.

Figure 6:
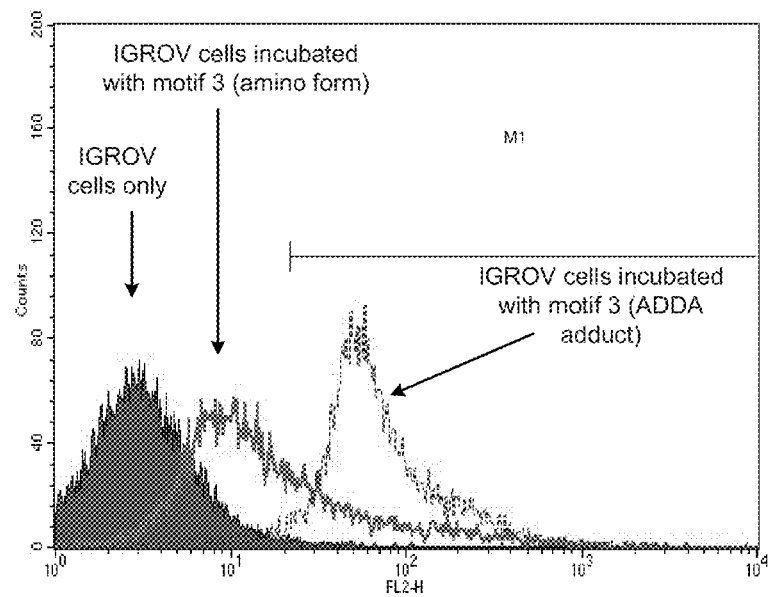
FIG. 6 shows flow cytometry results of ovarian cancer cell line IGROV (CD44+) incubated with Motif 3 (amino form and ADDA adduct) at 37° C. for 2 hours.

Cell Binding Assay. Ovarian cancer cell line IGROV (CD44+) was incubated with fluorescently labeled motif 3 (amino form and ADDA adduct) at 37° C. for 2 hours. After being washed 2 times, the cells were subjected to flow cytometry analysis. The flow cytometry histogram of FIG. 6 shows that the binding of motif 3 to IGROV cells is improved by the conjugation of ADDA ligand. The result clearly shows that the conjugation of ADDA to motif 3 improves its binding to IGROV cells.

Figure 16:
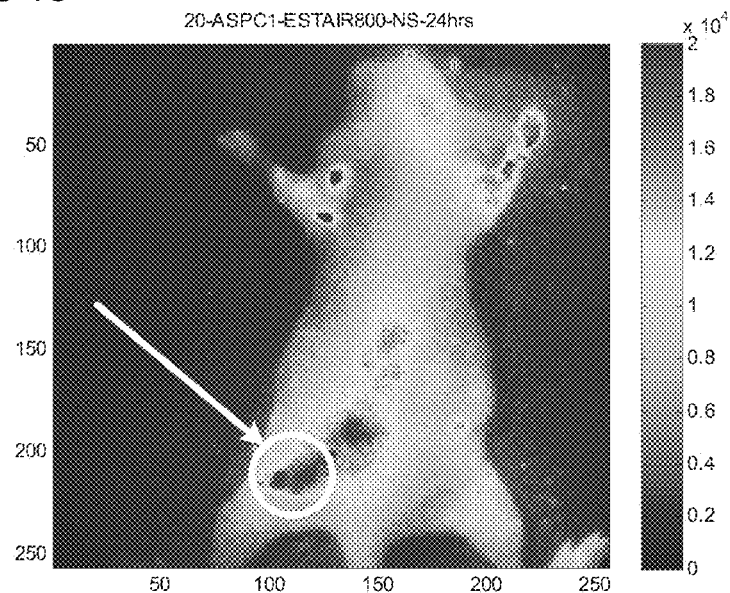
FIG. 16 shows the results of Near Infrared (NR) images of an IRdye 800-labelled ESTA-1 thioaptamer—gold nanoparticle binding in a mouse model of human pancreatic cancer.
Figure 17:
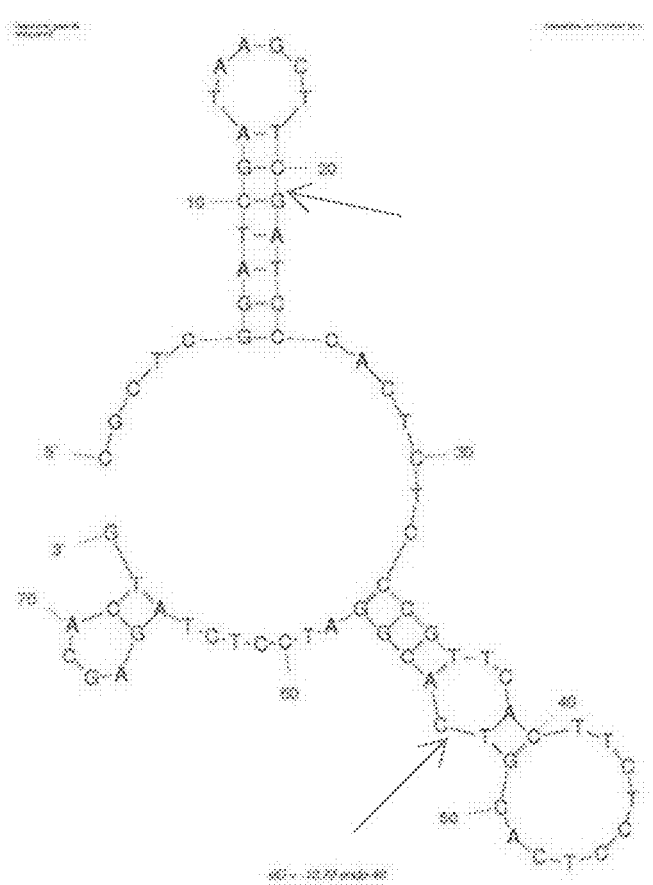
FIG. 17 shows the two dimensional stem-loop structure of the ESTA-1 thioaptamer.

Use of Thioaptamers in vivo. As just one example, FIG. 16 shows a near infrared image of a mouse with a human pancreatic cancer xenograph (circled) in which an IR800dye-labeled thioaptamer accumulates in the tumor. FIG. 17 shows the predicted two dimensional structure of the ESTA-1 thioaptamer sequence (SEQ. ID. 32). This in vivo test demonstrate that thioaptamers are sufficiently stable in vivo to survive the numerous circulatory cycles required for accumulation in a tumor and provides substantiation for their applicability to diagnosis and treatment of disease including cancer.

EXAMPLE 3

Click Chemistry

Figure 8:
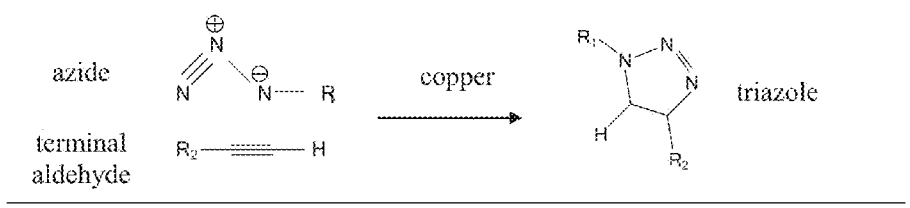
FIG. 8 shows the reaction of azides and alkynes to form triazoles in the presence of copper.
Figure 9:
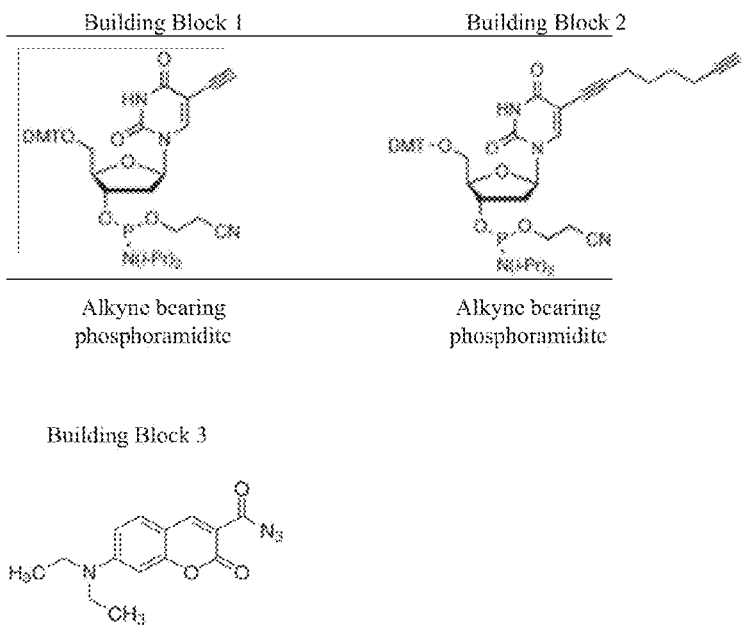
FIG. 9 shows examples of building blocks for azide click chemistry.
Figure 10A:
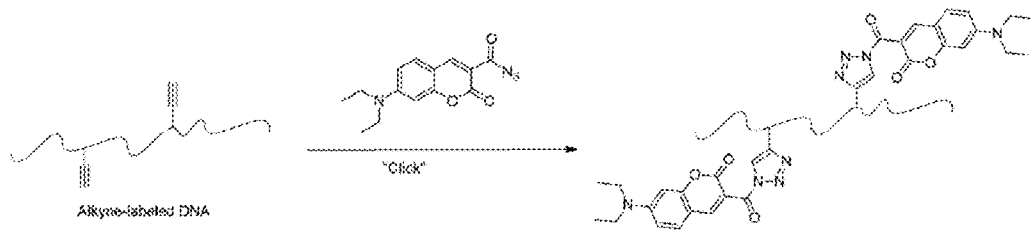
FIG. 10 shows an example of a click chemistry alkyne reaction.
Figure 10B:
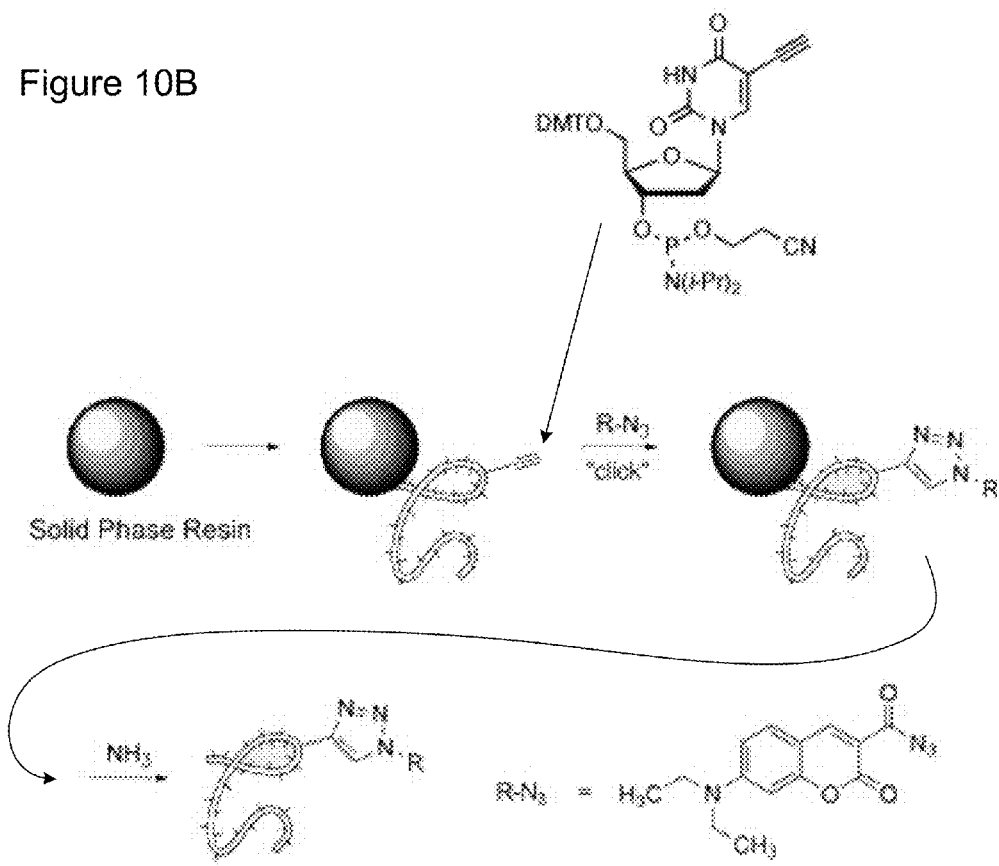

In another embodiment, libraries are constructed using click chemistry as an alternative to the amide coupling chemistry to introduce multiple, in silico selected, drug-like hits into the X-aptamers. Click chemistry is used to describe two step chemical reactions that involve copper-catalyzed triazole formation from an azide and an alkyne as shown in FIG. 8. As shown, the azides (R-N3) react with alkynes under copper catalysis to form triazoles by cycloaddition. The azide and alkyne moieties can be used interchangeably and either one can be used to tag the molecule of interest, with the other used for subsequent detection. The azides and alkynes are biologically unique, inert, stable, and extremely small and can be used to tag nucleotides, which remain acceptable substrates for the enzymes. X-aptamers have also been chemically synthesized to contain 5-ethynyl-dU, which, when reacted with X-azides, forms a triazole appended to the X-aptamer at the 5-X-dU residue. If only one type of X-azide is to be attached to a random aptamer, a library is created in which each position is a standard ODN base or a 5-alkynyl-dU. If the alkyne is not protected, the azides can be added before or after deprotection of the DNA. Addition before deprotection of DNA allows for directed attachment of several, possibly different, azide molecules to the ODN library at any position. To introduce the alkyne label, either thymidine-like alkynyl phosphoramidite building block 1 (5'-Dimethoxytrityl-5-ethynyl-2'-deoxyuridine, 3'-[(2-cyanoethyl)-(N,N-diisopropyl)]-phosphoramidite) or 2 (5'-Dimethoxytrityl-5-(octa-1,7-diynyl)-2'-deoxyuridine, 3'-[(2-cyanoethyl)-(N,N-diisopropyl)]-phosphoramidite) in FIG. 9 was incorporated into the oligonucleotides in Table 5 below using standard phosphoramidite chemistry. The azides are subsequently attached by click chemistry as shown in FIGS. 10A and B (showing the reaction on a bead). The coupling yield was excellent.

The click reaction on solid support was performed by shaking the resin (ODN-10, Table 5) with a solution of CuBr, tris(benzyltriazolylmethyl)amine (TBTA), sodium ascorbate, and the azide 3 (7-(Diethylamino)coumarin-3-carbonyl azide) (building block 3 of FIG. 9) or the azide 4-fluorescent dye Alexa® Fluor 555 azide (Cat. No. A20012, available from Life Technologies) (building block 4). After reaction, a portion of resin was packed in a new column and synthesis continued to yield ODN-11. The DNA was finally cleaved from the resin, and all protecting groups were removed by exposing the resin to ammonia.

TABLE 5

ODNS 1-11 EMPLOYED IN THE "CLICK" CHEMISTRY

| ODN | Sequence | SEQ. ID. |
|---|---|---|
| 1 | 5'-CGGCYGTTCATTYGGC-3' | 33 |
| 2 | 5'-CGGCTGTTCATTYGGC-3' | 34 |
| 3 | 5'-CGGcYGTTCATTYgGC-3' | 35 |
| 4 | 5'-CGGCTGTTCATTYGGC-3' | 36 |
| 5 | 5'-CGGCTGTTCATTYGGC-3' | 37 |
| 6 | 5'-TACGXCTCGXAGTA-3' | 38 |
| 7 | 5'-TaCGXCTCgXAGTA-3' | 39 |
| 8 | 5'-GGGGCACGTTTATCCGTCCCTCCTAGTGGCGXGCCCC-3' | 40 |
| 9 | 5'-GGGGCXCGTTTATCCGTCCCTCCTAGTGGCGTGCCCC-3' | 41 |

TABLE 5-continued

ODNS 1-11 EMPLOYED IN THE "CLICK" CHEMISTRY

| ODN Sequence | SEQ. ID. |
|---|---|
| 10[a] 5'-XAGTA-3' | |
| 11[b] 5'-TGTCTTGCcTCGGTTTtCgCTGTTgTCgTCCgCtTTCG TTCXAGTA-3' | 42 |

X = DNA nucleotide based on phosphoramidite 1;
Y = DNA nucleotide based on phosphoramidite 2;
a, t, c and g indicate 5'-monothioate linkage;
G and Y indicate 5'-dithioate linkage.
[a]Click reaction performed on resin.
[b]Oligonucleotide synthesis continued (adding 41 more bases) after click reaction performed on ODN-10.

Figure 11:
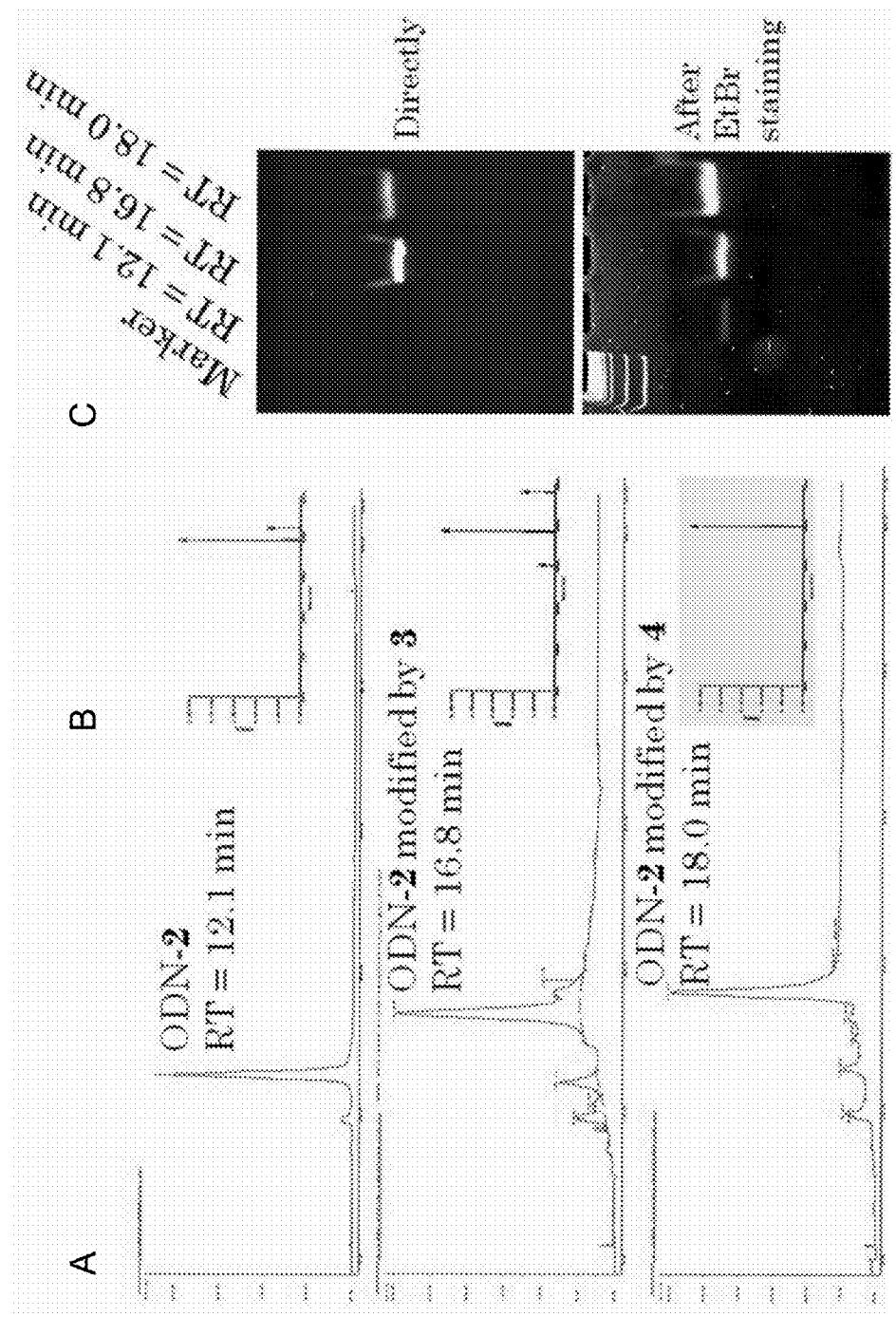
FIG. 11 shows the results of a time wise progression of click chemistry by HPLC (A), mass spectroscopy (B), and gel electrophoresis (C).

The click reaction was performed in solution after oligonucleotide deprotection. Treatment of the ODNs-1-9 with concentrated $NH_3$ cleaved the DNA from the resin. Under these conditions the base protecting groups were removed as well. The obtained DNA, bearing free alkynes, was subjected to the click reaction in solution (CuBr, TBTA, the azide 3 or 4), yielding the modified DNA. The modified ODNs, the products from click reaction, were analyzed by HPLC, mass spectrometry (MS), and PAGE-gel analysis. FIG. 11A shows HPLC traces for the crude click reactions of ODN-2 with azide 3 and 4. The click reactions have yielded greater than 90% as determined by the peak area. The click reaction products from these two reactions have longer retention times than free ODN-2 because a large hydrophobic molecule (azide 3 or 4) is conjugated. The click reaction products were analyzed by polyacrylamide gel electrophoresis as shown in FIG. 11C. The ODN-2 azide adducts are fluorescent without ethidium bromide staining after modification with azide 3 or 4. The identity of the click reaction products were confirmed by mass spectrometry (FIG. 11B). ODN-2 m/z: calculated 4965.3, observed 4969.6; ODN-2-Azide-3 adduct m/z: calculated 5251.6 observed 5229.8; ODN-2-azide-4 adduct m/z: calculated 5711.0, observed 5710.2.

DNA synthesis can be halted for the addition of a small molecule azide to a 5-alkynyl-dU base while the DNA is still attached to a CPG bead, and synthesis can be restarted with subsequent additions later in the sequence. This method allows for the directed attachment of several, possibly different, azide molecules to the ODN library at any position.

Thus enormously more complex libraries of X-aptamers may be created in which every base can have an amino-acid-like side-chain or a complex drug moiety. Rather than only use 4 bases or even 20 amino acid-like side-chains, virtually an unlimited range of chemical functional groups can be introduced into an X-aptamer that can fold into a unique 3D scaffold to present to the target protein multiple drug-like groups with an enormously more complex range of substituents.

EXAMPLE 4

Selection of X-Aptamer with Two Nucleotide Ligands

Considering the results of the equilibrium binding constants determined by the filter binding assay (Table 4), Motif 2 was selected in order to follow several molecular dynamics simulations of possible binding conformations interacting with CD44-HABD. The software AMBER12 (Case et al. AMBER12 (2012) UCSF) was used with the Molecular Dynamics Simulation protocol previously described herein.

Once the best binding model was obtained after the simulations, it was determined that a new pocket was accessible close to the cytosine 13 (SEQ ID 28, Table 3) and facing the major groove side. Considering that this cytosine is part of the G-C base-pair stabilizing the hairpin of Motif 2 (FIG. 4A, XA1), which plays an important role for the stability of the binding interaction, it was decided select a cytosine analogue as a new ligand in order to keep the G-C base-pair intact. The following three possible deoxycytidine analogs were selected based on the ability to base pair faithfully with dG with virtually no disruption of the normal duplex structure.

The deoxycytidine analogs shown below were obtained from Glen Research:

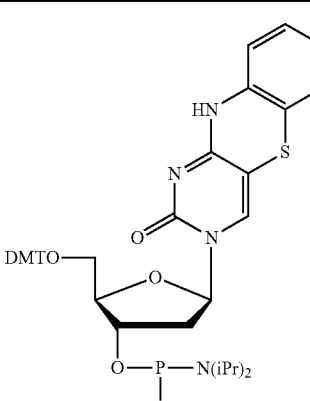

| Acronym | Structure | Chemical Name |
|---|---|---|
| tC | 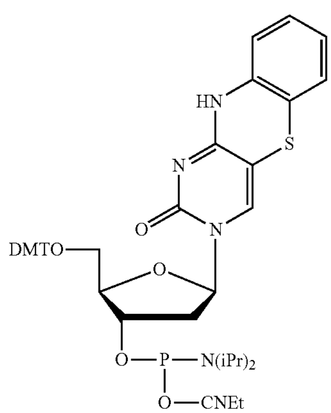 | tC-CE Phosphoramidite: a.k.a. 5'-O-(4,4'-Dimethoxytrityl)-1'-(1,3-diaza-2-oxophenothiazin-1-yl)-2'-deoxy-B-D-ribofuranosyl-3'-[(2-cyanoethyl)-(N,N-diisopropyl)]-phosphoramidite |

-continued

| Acronym | Structure | Chemical Name |
|---|---|---|
| tCo | 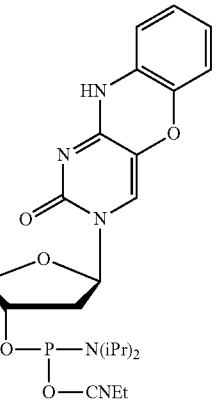 | tC °-CE Phosphoramidite: a.k.a. 5'-O-(4,4'-Dimethoxytrityl)-1'-(1,3-diaza-2-oxophenoxazin-1-yl)-2'-deoxy-B-D-ribofuranosyl-3'-[(2-cyanoethyl)-(N,N-diisopropyl)]-phosphoramidite |
| tCnitro | 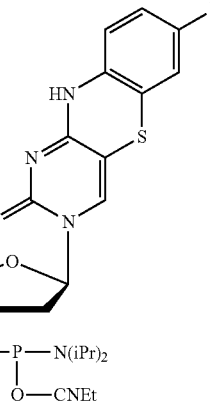 | tCnitro-CE Phosphoramidite: a.k.a. 5'-O-(4,4'-Dimethoxytrityl)-1'-(7-nitro-1,3-diaza-2-oxophenothiazin-1-yl)-2'-deoxy-B-D-ribofuranosyl-3'-[(2-cyanoethyl)-(N,N-diisopropyl)]-phosphoramidite |

The geometry of the three ligands were initially optimized with Gaussian03 (Frisch et al. 2004) using HF/6-31G* level of theory and then a single-point calculation (with the same level of theory) was performed to obtain the electrostatic potential. Fitting charges to the electrostatic potential were then performed with RESP (AMBER12 suite of programs). These new ligands were then incorporated into the model (CD44-HABD+motif2-ADDA-cytosine_analogue) and each model was followed by a molecular dynamics simulation of 50 ns. After these calculations, an X-aptamer model having ADDA and tCnitro ligands was determined to be most stable by molecular modeling.

EXAMPLE 5

Selection of X-Aptamer with Multiple Binding Moieties

The previous examples provide herein have shown that a small molecule drug (ADDA) can be randomly incorporated along with modified nucleotides into an X-aptamer. While the prior examples describe conjugation with one specific drug at a time, multiple drug hits can be randomly attached as well, to provide enhanced combinations of binding moieties. For example, more than one ligand can be attached by pausing the DNA synthesis for the addition of a ligand and subsequent DNA synthesis and coupling reactions. By using two or more chemical linkers in one root library, multiple drugs may be selectively incorporated. This methodology can be applied to most targets with a variety of small molecules to create highly chemically modified X-aptamers that have the combined characteristics of drug molecules, proteins and nucleic acids.

For example, both amidites with 5-dU ethynyl groups may be used to couple to small molecule azide leads with click chemistry as well as 5-amino dU phosphoramidites, which can be coupled with small molecule carboxylate leads with amide coupling reagents. The 5-dU ethynyl groups and 5-amino dU groups may be randomly placed into the X-aptamer backbone and stepwise conjugating both the azide leads and carboxylate leads to the bead library will produce an XA library with both leads (1-6 azides, 1-6 or more carboxylates on each oligonucleotide strand). Alternatively the DNA synthesizer can be stopped during a pooling step and click chemistry performed with different azide drug leads and resplitting the beads onto the synthesizer for further elongation and placing >2 different drugs on each XA. The goal of linking two or more drug fragments has been elusive because it is not possible to structural identify the best linker to attach the two drug fragments so that proper spacing and orientation is achieved. The XA method described herein avoids that problem since combinatorial chemistry can be used and the oligonucleotide scaffold allowed to form secondary and tertiary structural motifs that allow the most favorable separation and orientation of the multiple drug fragments.

EXAMPLE 6

Generation of Small Molecule-Aptamer "Two-Hit" Conjugates

Figure 18:
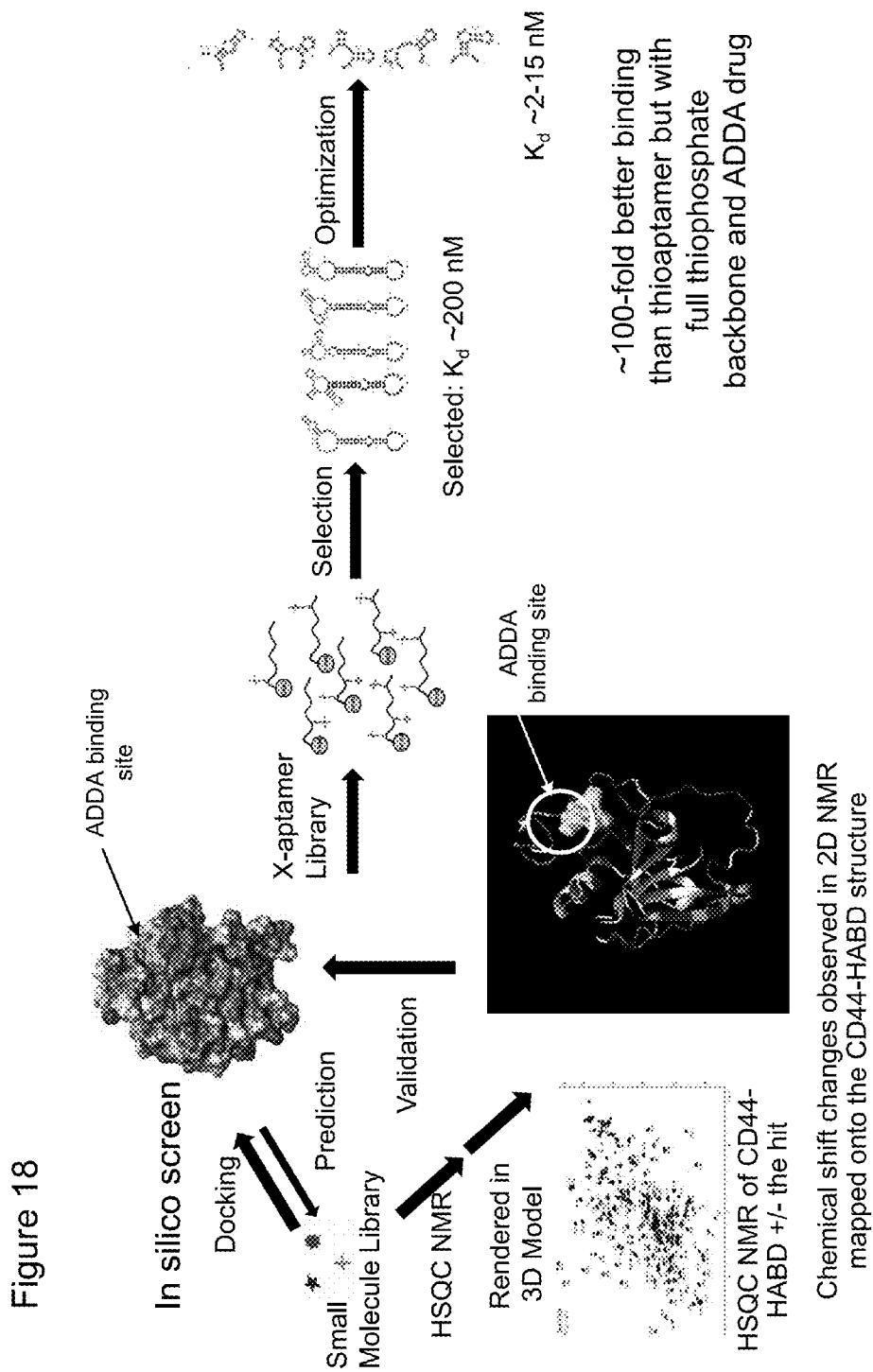
FIG. 18 shows one embodiment of a pathway for generating a drug bearing X-aptamer.

As shown in FIG. 18, in one embodiment a small molecule library is interrogated in silico by screening with computer docking of each member of the library (potentially millions) onto various binding sites of the protein. The tightest binding theoretical hits are selected and binding to the target protein (i.e. HABD CD44) is confirmed, such as by NMR. For example, $^{15}$N labeled protein can be used so that a 2D HSQC $^{15}$N-$^1$H NMR spectrum can be used to identify the individual amides signals that are perturbed in the presence of the drug. In the 3D backbone model inset to FIG. 18 those residues are highlighted that show the largest chemical shift perturbations upon drug binding—signifying the drug binding site (ADDA drug is circled). This validates the original model where the drug (circled) is shown in the space filling model.

As described previously herein, an XA library is then constructed with approximately 1,000,000 different sequences and different locations and numbers of drugs (i.e. ADDA molecules) attached to the beads. The bead library is selected and individual beads sequenced and $K_D$ measured. Optimization of the selected sequences is performed by modeling of the two and three dimensional structures of the binding domains and shortened motif sequences are prepared. In the example provided herein for CD44 binding, the resulting drug modified shortened aptamers showed much tighter binding to the protein, enhancing drug binding by 1,000,000 fold and aptamer alone binding by 100-fold. Where there is no entropic loss in orienting the conjugated drug and the linked oligonucleotide to the protein, it is predicted that the conjugate will attain $2 \times 10^{-3} \times 200 \times 10^{-9}$ or 0.4 nM binding affinity for the conjugate. Remarkably the actual binding affinity attained was 2 nM vs. the theoretically best affinity of 0.4 nM.

EXAMPLE 7

Dual-ligand CD44 X-aptamer Motifs

In order to enhance the affinity and selectivity of our next generation X-aptamers, by adding drug-like ligands or amino-acid like side chains to the bases, we devised a bead-based combinatorial library selection method in which one or more X-ligands can be linked to aptamers in a random fashion. By combining the one-bead, one-sequence thioaptamer selection method with the incorporation of pseudo-randomly placed bases that contain chemical linkers, additional binding X-ligands can be appended onto aptamers or thioaptamers to create a next-generation, X-aptamer library, and the best binding X-aptamers can be selected from this large pool of sequences. In one example, ligands were attached with amine-N-hydroxysuccinimide (NHS)-ester coupling to alter the binding properties of a thioaptamer specific to the CD44 hyaluronic acid binding domain (CD44-HABD). We have shown that such X-aptamers had strong binding to human cells expressing CD44 (found on stem cells and cancer cells) and showed the same pattern as that of anti-human CD44 antibody. To this end selected CD44 X-aptamers (motif 3 and motif 5 of Table 6) were shown to bind to human ovarian cancer IGROV cells overexpressing CD44. Cultured IGROV cells were incubated with Cy3-X-aptamers or FITC conjugated anti-human CD44 antibody. A blue nuclear counterstain was done by Hoechst 33342 and both motifs bound to membrane of IGROV cells with the same pattern as that of CD44 antibody (data not shown). These X-aptamers were selected with a small drug-like molecule attached randomly to the bead-based library. The drug ADDA (N-acetyl-2,3-dehydro-2-deoxyneuraminic acid) was selected as the lead compound because it bound in the hyaluronic acid (HA) binding pocket believed also to be the binding site of the originally selected thioaptamers.

Based on molecular dynamics calculations, tCnitro-CE Phosphoramidite was incorporated into the motif 2, motif 3 and motif 5 X-aptamers as another ligand for CD44 HABD (Table 6). We made 11 constructs with a C9 spacer and Cy3 at the 5' end. Each of them contains two different ligands, amino C2 dT (to which the ADDA drug is attached) and dCnitro.

TABLE 6

SEQUENCES OF X-APTAMER MOTIFS TESTED BY CELL BINDING ASSAY

| | | SEQ. ID. |
|---|---|---|
| Sequence for dual-ligand X-aptamer motif constructs based upon motifs 2, 3 and 5 | | |
| VI59A | 5'-CTGXTAGGGAACYAAGACGA-3' | 43 |
| VI59B | 5'-CTGTXAGGGAACYAAGACGA-3' | 44 |
| VI59C | 5'-CTGXTAGGGAACYAA-3' | 45 |
| VI59D | 5'-CTGTXAGGGAACYAA-3' | 46 |
| VI59E | 5'-CTGTXAGGGAAYCAAGACGA-3' | 47 |
| VI59F | 5'-CTGTXAGGGAAYCAA-3' | 48 |
| VI59G | 5'-GCGTGCAAYACCXCCATAGAGAC-3' | 49 |
| VI59H | 5'-GCCTGCAAGYAGXCCATAGACAC-3' | 50 |
| VI59I | 5'-GCCTGCAAGAYGXCCATAGACAC-3' | 51 |
| VI59J | 5'-GCCTGCAAGACYXCCATAGAGAC-3' | 52 |
| VI59K | 5'-AGATACAGTAAAYGXCCATAGACAC-3' | 53 |
| Sequences of the original motifs 2-5 | | |
| Motif 2 | 5'-CXGXTAGGGAACCAAGACGA-3' | 54 |
| Motif 3 | 5'-GCCTGCAAGACGXCCATAGACAC-3' | 55 |
| Motif 4 | 5'-GATCTGCAAXGTAACCATAGACA-3' | 56 |
| Motif 5 | 5'-AGAXACAGTAAACGXCCATAGACAC-3' | 57 |

Note:
X = amino modifier C2 dT;
Y = tCnitro-CE phosphoramidite

Figure 19:
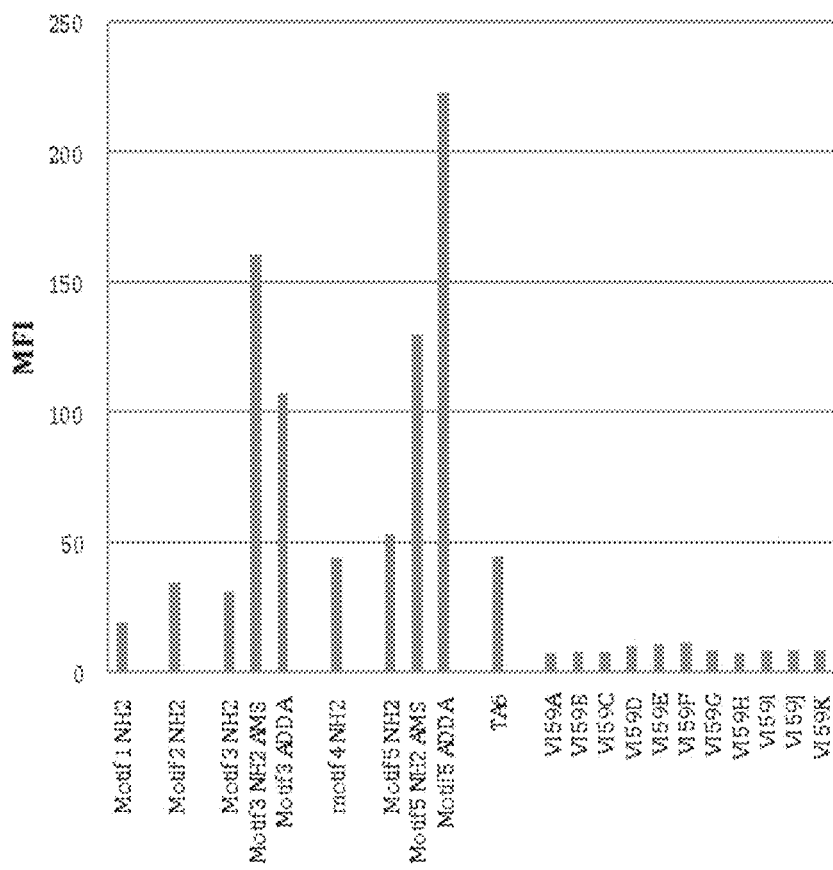
FIG. 19 presents data on Mean Fluorescence Intensity (MFI) of IGROV cells incubated with X-aptamer motifs at 37° C. for 2 hours.

The X-aptamer motifs of Table 6 were incubated with CD44 positive ovarian cancer cell line IGROV at 37° C. for 2 hours with the result shown in FIG. 19. Mean fluorescent intensity and % Gated cells of 10,000 cells were used to compare the relative binding affinity towards the new XA motifs: AMS: all monothioate backbone substitution; ADDA: N-Acetyl-2,3-dehydro-2-deoxyneuraminic acid (coupled to the motifs via amino modifier C2 dT).

Figure 20:
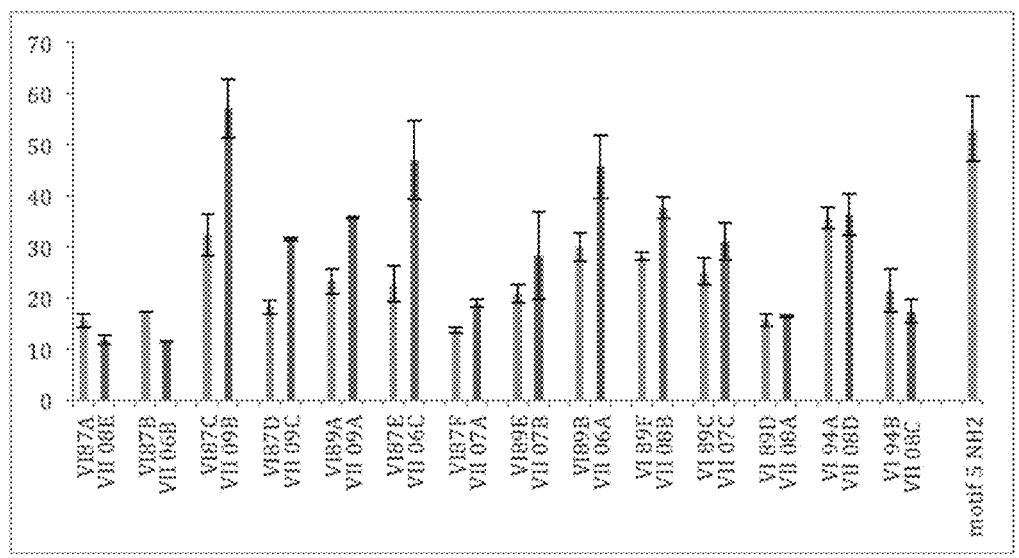
FIG. 20 presents data on Mean Fluorescence Intensity (MFI) of IGROV cells incubated with dithioated X-aptamer motifs at 37° C. for 2 hours.

Dithioate CD44 X-aptamer Our previous study indicated that X-aptamer motif 3 and motif 5 had strong binding to human ovarian cancer IGROV cells and shown the same pattern as that of anti-human CD44 antibody. We investigated the effect of a dithioate substitution replacing both nonlinking phosphoryl oxygens with sulfurs. Such modification of oligonucleotides can confer nuclease resistance as well as lead to the enhanced binding affinity. We made 14 dithioate X-aptamers (2 to 5 dithioates incorporated at various positions) based on the sequences of motif 3 and motif 5 (Table 6). The X-aptamer motifs (Table 7) were incubated with CD44 positive ovarian cancer cell line IGROV at 37° C. for 2 hours. Mean fluorescent intensity and % of positive cells of total 10,000 cells were used to compare the relative binding affinity among the XA motifs. Incubation with Amino-dT XAs are shown in the first bar of each set. Incubation with ADDA modified dithioate XAs are shown in the second bar of each set. In FIG. 20, the new sequences as named have the following substitutions: 6=dA thiophosphoramidite; 7=dC thiophosphoramidite; 8=dG-thiophosphoramidite; 9=dT thiophosphoramidite.

EXAMPLE 8

Further CD44 X-aptamer Substituents

In addition to ADDA, a second bead selection with a different drug—pteroic acid—was conducted which resulted in very similar sequences to the ADDA-drug aptamer. See FIG. 21.

EXAMPLE 9

Further X-aptamer Substituents

It has been demonstrated by certain of the present inventors that even conservative modifications such as introducing phosphorodithioate in place of phosphate can have profound beneficial effects on aptamer binding affinity. The approach of using greater chemical diversity can be greatly expanded by using the many chemically-modified DNA or RNA reagents currently available but not compatible with SELEX. According to the methods disclosed herein, virtually any modified nucleosides individually or in combination that provide favorable functional groups can be utilized to improve molecular interactions. These include positively-charged groups, hydrophobic groups, and amino acid side chains. Initial selections using amino acid side chains have shown tremendous promise.

Additional tested examples of chemically modified nucleotides for use in X-aptamers (X-As) include phosphorodithioates (1), 2'-O-methyl phosphorodithioates (2), deoxyuridine derivatives carrying aromatic amino acid side chains such as indole (3) or phenol (4), and deoxyuridines derivatives carrying positively charged amino acid side chains such as guanidine (5). Certain nucleotides that are commercially available as phosphoramidites for oligonucleotide synthesis are also of interest, including carboxy-dT from Glen Research (6) and 5-aminoallyl-dU from Berry & Assoc. (7). It has been demonstrated that X-aptamers incorporating (1) or (2) can provide significantly enhanced binding affinities without loss of specificity. More recently, we have shown that nucleotides modified with certain amino acid side chains can provide significantly enhanced aptamer binding. The above referenced modified nucleotides (1)-(7) are shown below:

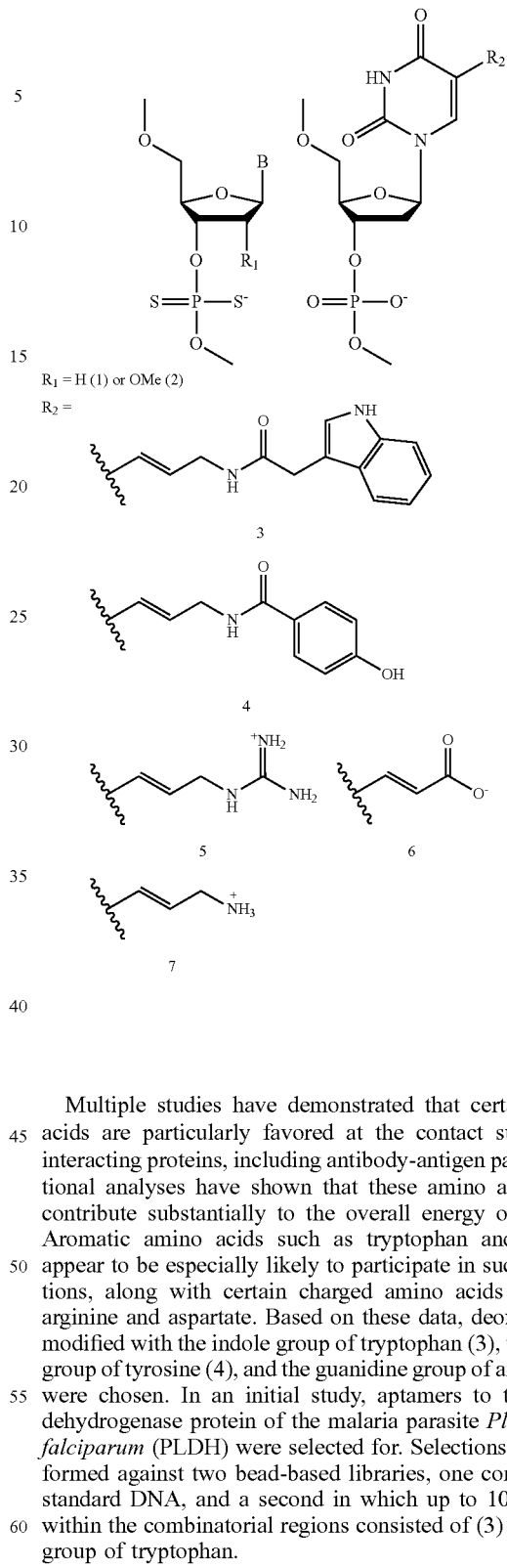

Multiple studies have demonstrated that certain amino acids are particularly favored at the contact surfaces of interacting proteins, including antibody-antigen pairs. Mutational analyses have shown that these amino acids often contribute substantially to the overall energy of binding. Aromatic amino acids such as tryptophan and tyrosine appear to be especially likely to participate in such interactions, along with certain charged amino acids including arginine and aspartate. Based on these data, deoxyuridines modified with the indole group of tryptophan (3), the phenol group of tyrosine (4), and the guanidine group of arginine (5) were chosen. In an initial study, aptamers to the lactate dehydrogenase protein of the malaria parasite *Plasmodium falciparum* (PLDH) were selected for. Selections were performed against two bead-based libraries, one consisting of standard DNA, and a second in which up to 10 positions within the combinatorial regions consisted of (3) the indole group of tryptophan.

No aptamers with detectable binding activity were recovered from the unmodified library. In contrast, multiple high affinity XAs were recovered from the indole-modified library. Individual XAs were resynthesized with appropriate indole modifications, and biolayer interferometry was used to estimate kinetic rate constants and equilibrium affinity constants. Many bound with $K_D$<10 nM, and several bound with estimated $K_D$<100 pM. Two of the isolated sequences are shown below with the modified deoxyuridines underlined:

PLDH-M106:

SEQ ID 68

5'-

GGTGTGCTGTGGCAGCGACGAAT<u>UU</u>CAAGGGC<u>U</u>TTT<u>UUU</u>C<u>U</u>GCAATCGT

TCCGTGCGGGAGCCTG-3'

PLDH-M86

SEQ ID 69

5'-

GGTGTGCTGTGGCAGCGACGATCGGTT<u>U</u>CATT<u>U</u>CCA<u>UUU</u>T<u>U</u>T<u>U</u>TCGT

TCCGTGCGGGAGCCTG-3'

All publications, patents and patent applications cited herein are hereby incorporated by reference as if set forth in their entirety herein. While this invention has been described with reference to illustrative embodiments, this description is not intended to be construed in a limiting sense. Various modifications and combinations of illustrative embodiments, as well as other embodiments of the invention, will be apparent to persons skilled in the art upon reference to the description. It is therefore intended that the appended claims encompass such modifications and enhancements.

We claim:

1. A method for isolating a target specific X-aptamer comprising:
   generating a primary one bead one unique oligonucleotide sequence library by a first split and pool bead synthesis using a programmed synthesizer;
   identifying an aptamer lead sequence by target binding and sequence determination and pseudo-randomly inserting chemical linker modified nucleotides into the aptamer lead sequence by a second split and pool bead synthesis;
   providing one or more X-ligands, wherein the X-ligands are known or predicted to bind to the target;
   generating a secondary one bead one unique oligonucleotide sequence X-aptamer library using a second split and pool bead synthesis wherein the X-aptamer library is generated by adding the one or more X-ligands to the aptamer lead sequence and linking the one or more X-ligands via the chemical linkers that had been pseudo-randomly inserted into the aptamer lead sequence thereby forming an X-aptamer library; and
   identifying a target specific X-aptamer sequence by target binding and sequence determination.

2. The method of claim 1, wherein the primary one bead one unique oligonucleotide sequence library is partially thio-modified or dithio-modified.

3. The method of claim 1, wherein one or more nucleotides are chemically modified in members of the primary one bead one unique oligonucleotide sequence library.

4. The method of claim 1, wherein the secondary chemical linker modified one bead one unique oligonucleotide sequence X-aptamer library is partially thio-modified or dithio-modified.

5. The method of claim 1, wherein the sequence determinations are performed by generation of unmodified oligonucleotide versions of the target binding sequences by polymerase chain reaction (PCR) amplification and nucleic acid sequencing.

6. The method of claim 1, wherein the chemical linker containing base is 5-[N-(2-aminoethyl)-3-(E)-acrylamido]-2'-deoxyuridine.

7. The method of claim 1 wherein the X-ligands are attached to the chemical linker prior to creation of the oligonucleotide library.

8. The method of claim 1 wherein the X-ligands are attached to the chemical linker between split and pool steps during creation of the oligonucleotide library.

9. The method of claim 1, wherein the X-ligands are coupled to the chemical linker after generation of the X-aptamer library.

10. The method of claim 1, wherein the X-ligands are added to nucleotides that incorporate X-groups by click chemistry.

11. The method of claim 10, wherein the X-ligands are added to nucleotides that incorporate ethynyl or azide X-groups by click chemistry.

12. The method of claim 1, wherein the X-ligands are added to nucleotides that incorporate carboxyl groups for coupling chemistry.

13. The method of claim 1, wherein the X-ligands are added to nucleotides that incorporate amine groups allowing for formation of an amide bond.

14. The method of claim 1, wherein X-ligands are selected by one or more of: in silico screening, high-throughput chemical screening of target binding site interactions, and NMR.

15. A method for isolating a target specific X-aptamer comprising:
generating a primary one bead one unique oligonucleotide sequence library by a first split and pool bead synthesis using a programmed synthesizer;
identifying an aptamer lead sequence by target binding and sequence determination;
generating a secondary chemical linker modified one bead one unique oligonucleotide sequence X-aptamer library using a second split and pool bead synthesis wherein at least one chemical linker containing base is pseudo-randomly inserted into the aptamer lead sequence and one or more X-ligands are linked to the at least one chemical linker thereby forming an X-ligand linked X-aptamer library;
identifying a target specific X-aptamer sequence by target binding and sequence determination; and
optimizing the identified target specific X-aptamer sequence by trimming of sequences that are determined to be non-target binding.

16. A method for isolating a target specific X-aptamer comprising:
generating a primary one bead one unique oligonucleotide sequence library by a first split and pool bead synthesis using a programmed synthesizer;
identifying an aptamer lead sequence by target binding and sequence determination;
generating a secondary chemical linker modified one bead one unique oligonucleotide sequence X-aptamer library using a second split and pool bead synthesis wherein at least one chemical linker containing base is pseudo-randomly inserted into the aptamer lead sequence and one or more X-ligands are linked to the at least one chemical linker thereby forming an X-ligand linked X-aptamer library; and
identifying a target specific X-aptamer sequence by target binding and sequence determination, wherein the X-ligand is a small molecule selected by in silico screening to bind to the target.

17. A method for isolating a target specific X-aptamer comprising:
generating a primary one bead one unique oligonucleotide sequence library by a first split and pool bead synthesis using a programmed synthesizer;
identifying a lead sequence by target binding and sequence determination;
generating a secondary one bead one unique oligonucleotide sequence X-aptamer library using a second split and pool one bead synthesis, wherein at least one or more X-ligands selected from ligands that are known or thought to bind to the target are linked to the secondary one bead one unique oligonucleotide sequence X-aptamer library using a chemical linker pseudo-randomly inserted into the aptamer lead sequence that provides for attachment of one or more X-ligands in randomized positions into the lead sequence thereby forming a secondary X-ligand linked X-aptamer library; and
identifying a target specific X-aptamer sequence by target binding and sequence determination.

* * * * *

SEQUENCE LISTING

```
<160> NUMBER OF SEQ ID NOS: 69

<210> SEQ ID NO 1
<211> LENGTH: 30
<212> TYPE: DNA
<213> ORGANISM: Artificial Sequence
<220> FEATURE:
<223> OTHER INFORMATION: synthetic

<400> SEQUENCE: 1
ccaaggcctg caagggaacc aaggacacag                                          30

<210> SEQ ID NO 2
<211> LENGTH: 30
<212> TYPE: DNA
<213> ORGANISM: artificial sequence
<220> FEATURE:
<223> OTHER INFORMATION: synthetic

<400> SEQUENCE: 2
ccaaggcatg caagggaacc aaggacacag                                          30

<210> SEQ ID NO 3
<211> LENGTH: 30
<212> TYPE: DNA
<213> ORGANISM: Artificial Sequence
<220> FEATURE:
<223> OTHER INFORMATION: aptamer

<400> SEQUENCE: 3
tgcagatgca aggtaaccat atccaaagca                                          30

<210> SEQ ID NO 4
<211> LENGTH: 30
<212> TYPE: DNA
<213> ORGANISM: Artificial Sequence
<220> FEATURE:
<223> OTHER INFORMATION: aptamer

<400> SEQUENCE: 4
cgtatgcaag gtgaaagcag cacaccaata                                          30

<210> SEQ ID NO 5
<211> LENGTH: 30
<212> TYPE: DNA
<213> ORGANISM: Artificial Sequence
<220> FEATURE:
<223> OTHER INFORMATION: aptamer
```

```
<400> SEQUENCE: 5
gcggcagtag ttgatcccga agcgttacga                                  30

<210> SEQ ID NO 6
<211> LENGTH: 30
<212> TYPE: DNA
<213> ORGANISM: Artificial Sequence
<220> FEATURE:
<223> OTHER INFORMATION: aptamer

<400> SEQUENCE: 6
ttgggacggt gttaaacgaa aggggacgac                                  30

<210> SEQ ID NO 7
<211> LENGTH: 30
<212> TYPE: DNA
<213> ORGANISM: Artificial Sequence
<220> FEATURE:
<223> OTHER INFORMATION: aptamer

<400> SEQUENCE: 7
ccaaggcctg caagggaacc aaggacacag                                  30

<210> SEQ ID NO 8
<211> LENGTH: 30
<212> TYPE: DNA
<213> ORGANISM: Artificial Sequence
<220> FEATURE:
<223> OTHER INFORMATION: aptamer
<220> FEATURE:
<221> NAME/KEY: misc_feature
<222> LOCATION: (1)..(1)
<223> OTHER INFORMATION: n = X = 5-(aminoethyl-3-acrylimido)-
      deoxyuridine
<220> FEATURE:
<221> NAME/KEY: misc_feature
<222> LOCATION: (18)..(18)
<223> OTHER INFORMATION: n = X = 5-(aminoethyl-3-acrylimido)-
      deoxyuridine

<400> SEQUENCE: 8
ngcagatcca gtaggtancc atatccaata                                  30

<210> SEQ ID NO 9
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: n = X =5-(aminoethyl-3-acrylimido)-
      deoxyuridine
<220> FEATURE:
<221> NAME/KEY: misc_feature
<222> LOCATION: (11)..(11)
<223> OTHER INFORMATION: n = X =5-(aminoethyl-3-acrylimido)-
      deoxyuridine

<400> SEQUENCE: 9
ttgggacgng ntaaacgaag gggacggtga                                  30

<210> SEQ ID NO 10
<211> LENGTH: 30
<212> TYPE: DNA
<213> ORGANISM: Artificial Sequence
<220> FEATURE:
```

```
<223> OTHER INFORMATION: synthetic
<220> FEATURE:
<221> NAME/KEY: misc_feature
<222> LOCATION: (1)..(2)
<223> OTHER INFORMATION: n = X = 5-(aminoethyl-3-acrylimido)-
      deoxyuridine
<220> FEATURE:
<221> NAME/KEY: misc_feature
<222> LOCATION: (7)..(7)
<223> OTHER INFORMATION: n = X = 5-(aminoethyl-3-acrylimido)-
      deoxyuridine
<220> FEATURE:
<221> NAME/KEY: misc_feature
<222> LOCATION: (11)..(11)
<223> OTHER INFORMATION: n = X = 5-(aminoethyl-3-acrylimido)-
      deoxyuridine
<220> FEATURE:
<221> NAME/KEY: misc_feature
<222> LOCATION: (14)..(15)
<223> OTHER INFORMATION: n = X = 5-(aminoethyl-3-acrylimido)-
      deoxyuridine
<220> FEATURE:
<221> NAME/KEY: misc_feature
<222> LOCATION: (19)..(19)
<223> OTHER INFORMATION: n = X = 5-(aminoethyl-3-acrylimido)-
      deoxyuridine
<220> FEATURE:
<221> NAME/KEY: misc_feature
<222> LOCATION: (21)..(21)
<223> OTHER INFORMATION: n = X = 5-(aminoethyl-3-acrylimido)-
      deoxyuridine
<220> FEATURE:
<221> NAME/KEY: misc_feature
<222> LOCATION: (24)..(24)
<223> OTHER INFORMATION: n = X = 5-(aminoethyl-3-acrylimido)-
      deoxyuridine
<220> FEATURE:
<221> NAME/KEY: misc_feature
<222> LOCATION: (28)..(29)
<223> OTHER INFORMATION: n = X = 5-(aminoethyl-3-acrylimido)-
      deoxyuridine

<400> SEQUENCE: 10
nnaaganaca naanngaang naanacanng                                      30

<210> SEQ ID NO 11
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: n = X = 5-(aminoethyl-3-acrylimido)-
      deoxyuridine
<220> FEATURE:
<221> NAME/KEY: misc_feature
<222> LOCATION: (21)..(21)
<223> OTHER INFORMATION: n = X = 5-(aminoethyl-3-acrylimido)-
      deoxyuridine
<220> FEATURE:
<221> NAME/KEY: misc_feature
<222> LOCATION: (28)..(28)
<223> OTHER INFORMATION: n = X = 5-(aminoethyl-3-acrylimido)-
      deoxyuridine

<400> SEQUENCE: 11
ccaagatcca ntagacgacc naatccanga                                      30

<210> SEQ ID NO 12
<211> LENGTH: 30
<212> TYPE: DNA
<213> ORGANISM: Artificial Sequence
<220> FEATURE:
```

```
<223> OTHER INFORMATION: synthetic
<220> FEATURE:
<221> NAME/KEY: misc_feature
<222> LOCATION: (1)..(2)
<223> OTHER INFORMATION: n = X = 5-(aminoethyl-3-acrylimido)-
      deoxyuridine
<220> FEATURE:
<221> NAME/KEY: misc_feature
<222> LOCATION: (9)..(9)
<223> OTHER INFORMATION: n = X = 5-(aminoethyl-3-acrylimido)-
      deoxyuridine
<220> FEATURE:
<221> NAME/KEY: misc_feature
<222> LOCATION: (11)..(11)
<223> OTHER INFORMATION: n = X = 5-(aminoethyl-3-acrylimido)-
      deoxyuridine

<400> SEQUENCE: 12
nnaagatcng ntagggaacc aagacgacag                                    30

<210> SEQ ID NO 13
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = X = 5-(aminoethyl-3-acrylimido)-
      deoxyuridine

<400> SEQUENCE: 13
ngcagatctg caagggaacc aaggacacta                                    30

<210> SEQ ID NO 14
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (28)..(28)
<223> OTHER INFORMATION: n = X = 5-(aminoethyl-3-acrylimido)-
      deoxyuridine

<400> SEQUENCE: 14
ccaaggcctg caagggaacc aagtccanta                                    30

<210> SEQ ID NO 15
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: n = X = 5-(aminoethyl-3-acrylimido)-
      deoxyuridine

<400> SEQUENCE: 15
ttggggcctg caagacgncc atagacacag                                    30

<210> SEQ ID NO 16
<211> LENGTH: 30
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (1)..(1)
<223> OTHER INFORMATION: n = X = 5-(aminoethyl-3-acrylimido)-
      deoxyuridine
<220> FEATURE:
<221> NAME/KEY: misc_feature
<222> LOCATION: (7)..(7)
<223> OTHER INFORMATION: n = X = 5-(aminoethyl-3-acrylimido)-
      deoxyuridine
<220> FEATURE:
<221> NAME/KEY: misc_feature
<222> LOCATION: (18)..(18)
<223> OTHER INFORMATION: n = X = 5-(aminoethyl-3-acrylimido)-
      deoxyuridine

<400> SEQUENCE: 16
ngcaganaca gtaaacgncc atagacacag                                            30

<210> SEQ ID NO 17
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (21)..(21)
<223> OTHER INFORMATION: n = X = 5-(aminoethyl-3-acrylimido)-
      deoxyuridine
<220> FEATURE:
<221> NAME/KEY: misc_feature
<222> LOCATION: (28)..(28)
<223> OTHER INFORMATION: n = X = 5-(aminoethyl-3-acrylimido)-
      deoxyuridine

<400> SEQUENCE: 17
ttggggcctg caagacgacc naaacganga                                            30

<210> SEQ ID NO 18
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n = X = 5-(aminoethyl-3-acrylimido)-
      deoxyuridine
<220> FEATURE:
<221> NAME/KEY: misc_feature
<222> LOCATION: (11)..(11)
<223> OTHER INFORMATION: n = X = 5-(aminoethyl-3-acrylimido)-
      deoxyuridine
<220> FEATURE:
<221> NAME/KEY: misc_feature
<222> LOCATION: (15)..(15)
<223> OTHER INFORMATION: n = X = 5-(aminoethyl-3-acrylimido)-
      deoxyuridine

<400> SEQUENCE: 18
nnaagacgca ntaangaacc aaggacgtga                                            30

<210> SEQ ID NO 19
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
```

```
<223> OTHER INFORMATION: n = X = 5-(aminoethyl-3-acrylimido)-
      deoxyuridine
<220> FEATURE:
<221> NAME/KEY: misc_feature
<222> LOCATION: (11)..(11)
<223> OTHER INFORMATION: n = X = 5-(aminoethyl-3-acrylimido)-
      deoxyuridine
<220> FEATURE:
<221> NAME/KEY: misc_feature
<222> LOCATION: (18)..(18)
<223> OTHER INFORMATION: n = X = 5-(aminoethyl-3-acrylimido)-
      deoxyuridine
<220> FEATURE:
<221> NAME/KEY: misc_feature
<222> LOCATION: (27)..(27)
<223> OTHER INFORMATION: n = X = 5-(aminoethyl-3-acrylimido)-
      deoxyuridine

<400> SEQUENCE: 19
ccaagatcng naaggtancc ggggacng                                         28

<210> SEQ ID NO 20
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n = X = 5-(aminoethyl-3-acrylimido)-
      deoxyuridine
<220> FEATURE:
<221> NAME/KEY: misc_feature
<222> LOCATION: (14)..(14)
<223> OTHER INFORMATION: n = X = 5-(aminoethyl-3-acrylimido)-
      deoxyuridine

<400> SEQUENCE: 20
nnaagatctg caangtaacc atagacacag                                       30

<210> SEQ ID NO 21
<211> LENGTH: 28
<212> TYPE: DNA
<213> ORGANISM: Artificial Sequence
<220> FEATURE:
<223> OTHER INFORMATION: synthetic

<400> SEQUENCE: 21
ttggggccca gtaggtaacc ggggacag                                         28

<210> SEQ ID NO 22
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: n = X = 5-(aminoethyl-3-acrylimido)-
      deoxyuridine
<220> FEATURE:
<221> NAME/KEY: misc_feature
<222> LOCATION: (25)..(25)
<223> OTHER INFORMATION: n = X = 5-(aminoethyl-3-acrylimido)-
      deoxyuridine

<400> SEQUENCE: 22
ttgggacgta agtaangggg gacanga                                          27
```

```
<210> SEQ ID NO 23
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n = X = 5-(aminoethyl-3-acrylimido)-
      deoxyuridine
<220> FEATURE:
<221> NAME/KEY: misc_feature
<222> LOCATION: (9)..(9)
<223> OTHER INFORMATION: n = X = 5-(aminoethyl-3-acrylimido)-
      deoxyuridine
<220> FEATURE:
<221> NAME/KEY: misc_feature
<222> LOCATION: (11)..(11)
<223> OTHER INFORMATION: n = X = 5-(aminoethyl-3-acrylimido)-
      deoxyuridine
<220> FEATURE:
<221> NAME/KEY: misc_feature
<222> LOCATION: (16)..(16)
<223> OTHER INFORMATION: n = X = 5-(aminoethyl-3-acrylimido)-
      deoxyuridine

<400> SEQUENCE: 23
nnaaggccng ntaaangata tccacta                                          27

<210> SEQ ID NO 24
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = X = 5-(aminoethyl-3-acrylimido)-
      deoxyuridine

<400> SEQUENCE: 24
ngcagatctg caagggaaag atagacacag                                       30

<210> SEQ ID NO 25
<211> LENGTH: 22
<212> TYPE: DNA
<213> ORGANISM: Artificial Sequence
<220> FEATURE:
<223> OTHER INFORMATION: synthetic

<400> SEQUENCE: 25
gagattcatc acgcgcatag tc                                               22

<210> SEQ ID NO 26
<211> LENGTH: 21
<212> TYPE: DNA
<213> ORGANISM: Artificial Sequence
<220> FEATURE:
<223> OTHER INFORMATION: synthetic

<400> SEQUENCE: 26
cgactatgcg atgatgtctt c                                                21

<210> SEQ ID NO 27
<211> LENGTH: 20
<212> TYPE: DNA
<213> ORGANISM: Artificial Sequence
<220> FEATURE:
<223> OTHER INFORMATION: synthetic
```

<400> SEQUENCE: 27
aagggaacca aggacactac                                              20

<210> SEQ ID NO 28
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n = X = 5-(aminoethyl-3-acrylimido)-
      deoxyuridine
<220> FEATURE:
<221> NAME/KEY: misc_feature
<222> LOCATION: (4)..(4)
<223> OTHER INFORMATION: n = X = 5-(aminoethyl-3-acrylimido)-
      deoxyuridine

<400> SEQUENCE: 28
cngntaggga accaagacga                                              20

<210> SEQ ID NO 29
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: n = X = 5-(aminoethyl-3-acrylimido)-
      deoxyuridine

<400> SEQUENCE: 29
gcctgcaaga cgnccataga cac                                          23

<210> SEQ ID NO 30
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: n = X = 5-(aminoethyl-3-acrylimido)-
      deoxyuridine

<400> SEQUENCE: 30
gatctgcaan gtaaccatag aca                                          23

<210> SEQ ID NO 31
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n = X = 5-(aminoethyl-3-acrylimido)-
      deoxyuridine
<220> FEATURE:
<221> NAME/KEY: misc_feature
<222> LOCATION: (15)..(15)
<223> OTHER INFORMATION: n = X = 5-(aminoethyl-3-acrylimido)-
      deoxyuridine

```
<400> SEQUENCE: 31
aganacagta aacgnccata gacac                                          25

<210> SEQ ID NO 32
<211> LENGTH: 73
<212> TYPE: DNA
<213> ORGANISM: Artificial Sequence
<220> FEATURE:
<223> OTHER INFORMATION: synthetic

<400> SEQUENCE: 32
cgctcggatc gataagcttc gatcccactc tcccgttcac ttctcctcac gtcacggatc    60
ctctagagca ctg                                                       73

<210> SEQ ID NO 33
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = Y = thymidine-like alkynyl phosphoramidite
      building block 2 with 5'-dithioate linkage
<220> FEATURE:
<221> NAME/KEY: misc_feature
<222> LOCATION: (13)..(13)
<223> OTHER INFORMATION: n = Y = thymidine-like alkynyl phosphoramidite
      building block 2 with 5'-dithioate linkage

<400> SEQUENCE: 33
cggcngttca ttnggc                                                    16

<210> SEQ ID NO 34
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: thymidine-like alkynyl phosphoramidite building
      block 2 with 5'-dithioate linkage

<400> SEQUENCE: 34
cggctgttca ttnggc                                                    16

<210> SEQ ID NO 35
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n = c with 5'-monothioate linkage
<220> FEATURE:
<221> NAME/KEY: misc_feature
<222> LOCATION: (5)..(5)
<223> OTHER INFORMATION: n = Y which is thymidine-like alkynyl
      phosphoramidite building block 2 with 5'-dithioate linkage.
<220> FEATURE:
<221> NAME/KEY: misc_feature
<222> LOCATION: (13)..(13)
<223> OTHER INFORMATION: n = Y which is thymidine-like alkynyl
      phosphoramidite building block 2 with  5'-dithioate linkage.
<220> FEATURE:
```

```
<221> NAME/KEY: misc_feature
<222> LOCATION: (14)..(14)
<223> OTHER INFORMATION: n = g with 5'-monothioate linkage

<400> SEQUENCE: 35
cggnngttca ttnngc                                                    16

<210> SEQ ID NO 36
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n = G with 5'-dithioate linkage.
<220> FEATURE:
<221> NAME/KEY: misc_feature
<222> LOCATION: (13)..(13)
<223> OTHER INFORMATION: n = Y which is thymidine-like alkynyl
      phosphoramidite building block 2 with 5'-dithioate linkage.

<400> SEQUENCE: 36
cggctnttca ttnggc                                                    16

<210> SEQ ID NO 37
<211> LENGTH: 16
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n = G with 5'-dithioate linkage.
<220> FEATURE:
<221> NAME/KEY: misc_feature
<222> LOCATION: (13)..(13)
<223> OTHER INFORMATION: n = Y which is thymidine-like alkynyl
      phosphoramidite building block 2 with 5'-dithioate linkage.

<400> SEQUENCE: 37
cggctnttca ttnggc                                                    16

<210> SEQ ID NO 38
<211> LENGTH: 14
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = X = thymidine-like alkynyl phosphoramidite
      building block 1
<220> FEATURE:
<221> NAME/KEY: misc_feature
<222> LOCATION: (10)..(10)
<223> OTHER INFORMATION: n = X = thymidine-like alkynyl phosphoramidite
      building block 1

<400> SEQUENCE: 38
tacgnctcgn agta                                                      14

<210> SEQ ID NO 39
<211> LENGTH: 14
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (2)..(2)
<223> OTHER INFORMATION: n = a with 5'-monothioate linkage
<220> FEATURE:
<221> NAME/KEY: misc_feature
<222> LOCATION: (5)..(5)
<223> OTHER INFORMATION: n = X =  thymidine-like alkynyl phosphoramidite
      building block 1
<220> FEATURE:
<221> NAME/KEY: misc_feature
<222> LOCATION: (9)..(9)
<223> OTHER INFORMATION: n = g with 5'-monothioate linkage
<220> FEATURE:
<221> NAME/KEY: misc_feature
<222> LOCATION: (10)..(10)
<223> OTHER INFORMATION: n = X =  thymidine-like alkynyl phosphoramidite
      building block 1

<400> SEQUENCE: 39
tncgnctcnn agta                                                          14

<210> SEQ ID NO 40
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (32)..(32)
<223> OTHER INFORMATION: n = X = thymidine-like alkynyl phosphoramidite
      building block 1

<400> SEQUENCE: 40
ggggcacgtt tatccgtccc tcctagtggc gngcccc                                  37

<210> SEQ ID NO 41
<211> LENGTH: 37
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: n = X = thymidine-like alkynyl phosphoramidite
      building block 1

<400> SEQUENCE: 41
ggggcncgtt tatccgtccc tcctagtggc gtgcccc                                  37

<210> SEQ ID NO 42
<211> LENGTH: 46
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: n = c with 5'-monothioate linkage
<220> FEATURE:
<221> NAME/KEY: misc_feature
<222> LOCATION: (17)..(17)
<223> OTHER INFORMATION: n = t with 5'-monothioate linkage
<220> FEATURE:
<221> NAME/KEY: misc_feature
<222> LOCATION: (19)..(19)
<223> OTHER INFORMATION: n = g with 5'-monothioate linkage
<220> FEATURE:
<221> NAME/KEY: misc_feature
<222> LOCATION: (25)..(25)
```

```
<223> OTHER INFORMATION: n = g with 5'-monothioate linkage
<220> FEATURE:
<221> NAME/KEY: misc_feature
<222> LOCATION: (28)..(28)
<223> OTHER INFORMATION: n = g with 5'-monothioate linkage
<220> FEATURE:
<221> NAME/KEY: misc_feature
<222> LOCATION: (32)..(32)
<223> OTHER INFORMATION: n = g with 5'-monothioate linkage
<220> FEATURE:
<221> NAME/KEY: misc_feature
<222> LOCATION: (42)..(42)
<223> OTHER INFORMATION: n = X which is thymidine-like alkynyl
      phosphoramidite building block 1

<400> SEQUENCE: 42
tgtcttgcnt cggtttncnc tgttntcntc cnctttcgtt cnagta                46

<210> SEQ ID NO 43
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n = X = amino modifier C2 dT
<220> FEATURE:
<221> NAME/KEY: misc_feature
<222> LOCATION: (13)..(13)
<223> OTHER INFORMATION: n = Y = tCnitro-CE phosphoramidite

<400> SEQUENCE: 43
ctgntaggga acnaagacga                                             20

<210> SEQ ID NO 44
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = X = amino modifier C2 dT
<220> FEATURE:
<221> NAME/KEY: misc_feature
<222> LOCATION: (13)..(13)
<223> OTHER INFORMATION: n = Y = tCnitro-CE phosphoramidite

<400> SEQUENCE: 44
ctgtnaggga acnaagacga                                             20

<210> SEQ ID NO 45
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n = X =amino modifier C2 dT
<220> FEATURE:
<221> NAME/KEY: misc_feature
<222> LOCATION: (13)..(13)
<223> OTHER INFORMATION: n = Y = tCnitro-CE phosphoramidite

<400> SEQUENCE: 45
ctgntaggga acnaa                                                  15
```

<210> SEQ ID NO 46
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = X = amino modifier C2 dT
<220> FEATURE:
<221> NAME/KEY: misc_feature
<222> LOCATION: (13)..(13)
<223> OTHER INFORMATION: n = Y = tCnitro-CE phosphoramidite

<400> SEQUENCE: 46
ctgtnaggga acnaa                                                        15

<210> SEQ ID NO 47
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = X = amino modifier C2 dT
<220> FEATURE:
<221> NAME/KEY: misc_feature
<222> LOCATION: (12)..(12)
<223> OTHER INFORMATION: n = Y = tCnitro-CE phosphoramidite

<400> SEQUENCE: 47
ctgtnaggga ancaagacga                                                   20

<210> SEQ ID NO 48
<211> LENGTH: 15
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: n = X = amino modifier C2 dT
<220> FEATURE:
<221> NAME/KEY: misc_feature
<222> LOCATION: (12)..(12)
<223> OTHER INFORMATION: n = Y = tCnitro-CE phosphoramidite

<400> SEQUENCE: 48
ctgtnaggga ancaa                                                        15

<210> SEQ ID NO 49
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: n = Y = tCnitro-CE phosphoramidite
<220> FEATURE:
<221> NAME/KEY: misc_feature
<222> LOCATION: (13)..(13)
<223> OTHER INFORMATION: n = X = amino modifier C2 dT

<400> SEQUENCE: 49
gcgtgcaana ccnccataga gac                                               23

```
<210> SEQ ID NO 50
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: n = Y = tCnitro-CE phosphoramidite
<220> FEATURE:
<221> NAME/KEY: misc_feature
<222> LOCATION: (13)..(13)
<223> OTHER INFORMATION: n = X = amino modifier C2 dT

<400> SEQUENCE: 50
gcctgcaagn agnccataga cac                                          23

<210> SEQ ID NO 51
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (11)..(11)
<223> OTHER INFORMATION: n = Y = tCnitro-CE phosphoramidite
<220> FEATURE:
<221> NAME/KEY: misc_feature
<222> LOCATION: (13)..(13)
<223> OTHER INFORMATION: n = X = amino modifier C2 dT

<400> SEQUENCE: 51
gcctgcaaga ngnccataga cac                                          23

<210> SEQ ID NO 52
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: n -= Y = tCnitro-CE phosphoramidite
<220> FEATURE:
<221> NAME/KEY: misc_feature
<222> LOCATION: (13)..(13)
<220> FEATURE:
<221> NAME/KEY: misc_feature
<222> LOCATION: (13)..(13)
<223> OTHER INFORMATION: n is a, c, g, or t

<400> SEQUENCE: 52
gcctgcaaga cnnccataga gac                                          23

<210> SEQ ID NO 53
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: n = Y = tCnitro-CE phosphoramidite
<220> FEATURE:
<221> NAME/KEY: misc_feature
<222> LOCATION: (15)..(15)
<223> OTHER INFORMATION: n = X = amino modifier C2 dT
```

-continued

<400> SEQUENCE: 53
agatacagta aangnccata gacac                                          25

<210> SEQ ID NO 54
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: n = X = amino modifier C2 dT
<220> FEATURE:
<221> NAME/KEY: misc_feature
<222> LOCATION: (4)..(4)
<223> OTHER INFORMATION: n = X = amino modifier C2 dT

<400> SEQUENCE: 54
cngntaggga accaagacga                                                20

<210> SEQ ID NO 55
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (13)..(13)
<223> OTHER INFORMATION: n = X = amino modifier C2 dT

<400> SEQUENCE: 55
gcctgcaaga cgnccataga cac                                            23

<210> SEQ ID NO 56
<211> LENGTH: 23
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (10)..(10)
<223> OTHER INFORMATION: n = X = amino modifier C2 dT

<400> SEQUENCE: 56
gatctgcaan gtaaccatag aca                                            23

<210> SEQ ID NO 57
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: n = X = amino modifier C2 dT
<220> FEATURE:
<221> NAME/KEY: misc_feature
<222> LOCATION: (15)..(15)
<223> OTHER INFORMATION: n = X = amino modifier C2 dT

<400> SEQUENCE: 57
aganacagta aacgnccata gacac                                          25

<210> SEQ ID NO 58

```
<211> LENGTH: 20
<212> TYPE: DNA
<213> ORGANISM: Artificial Sequence
<220> FEATURE:
<223> OTHER INFORMATION: synthetic

<400> SEQUENCE: 58
aagggaacca aggacactac                                                    20

<210> SEQ ID NO 59
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n = X =amino modifier C2 dT
<220> FEATURE:
<221> NAME/KEY: misc_feature
<222> LOCATION: (9)..(9)
<223> OTHER INFORMATION: n = X =amino modifier C2 dT
<220> FEATURE:
<221> NAME/KEY: misc_feature
<222> LOCATION: (11)..(11)
<223> OTHER INFORMATION: n = X =amino modifier C2 dT

<400> SEQUENCE: 59
nnaagacgng naagggaacc aaggacacta                                         30

<210> SEQ ID NO 60
<211> LENGTH: 29
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (8)..(8)
<223> OTHER INFORMATION: n = X = amino modifier C2 dT
<220> FEATURE:
<221> NAME/KEY: misc_feature
<222> LOCATION: (10)..(10)
<223> OTHER INFORMATION: n = X = amino modifier C2 dT

<400> SEQUENCE: 60
taagacgngn aagggaacca aggacacta                                          29

<210> SEQ ID NO 61
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: n = X = amino modifier C2 dT
<220> FEATURE:
<221> NAME/KEY: misc_feature
<222> LOCATION: (11)..(11)
<223> OTHER INFORMATION: n = X = amino modifier C2 dT

<400> SEQUENCE: 61
ccaagacgng ntaaggaacc aagacgacta                                         30

<210> SEQ ID NO 62
<211> LENGTH: 30
<212> TYPE: DNA
<213> ORGANISM: Artificial Sequence
```

```
<220> FEATURE:
<223> OTHER INFORMATION: synthetic
<220> FEATURE:
<221> NAME/KEY: misc_feature
<222> LOCATION: (9)..(9)
<223> OTHER INFORMATION: n = X = amino modifier C2 dT
<220> FEATURE:
<221> NAME/KEY: misc_feature
<222> LOCATION: (11)..(11)
<223> OTHER INFORMATION: n = X = amino modifier C2 dT

<400> SEQUENCE: 62
ccaagacgng ntagggaacc aagacgacta                                    30

<210> SEQ ID NO 63
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (18)..(18)
<223> OTHER INFORMATION: n = X = amino modifier C2 dT

<400> SEQUENCE: 63
ttggggcctg caagacgncc atagacacag                                    30

<210> SEQ ID NO 64
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n = X = amino modifier C2 dT
<220> FEATURE:
<221> NAME/KEY: misc_feature
<222> LOCATION: (14)..(14)
<223> OTHER INFORMATION: n = X = amino modifier C2 dT

<400> SEQUENCE: 64
nnaagatctg caangtaacc atagacacag                                    30

<210> SEQ ID NO 65
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n = X = amino modifier C2 dT
<220> FEATURE:
<221> NAME/KEY: misc_feature
<222> LOCATION: (18)..(18)
<223> OTHER INFORMATION: n = X = amino modifier C2 dT
<220> FEATURE:
<221> NAME/KEY: misc_feature
<222> LOCATION: (24)..(24)
<223> OTHER INFORMATION: n = X = amino modifier C2 dT
<220> FEATURE:
<221> NAME/KEY: misc_feature
<222> LOCATION: (28)..(28)
<223> OTHER INFORMATION: n = X = amino modifier C2 dT

<400> SEQUENCE: 65
nnaagatcca gtagacgncc atanacanta                                    30
```

```
<210> SEQ ID NO 66
<211> LENGTH: 29
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (17)..(17)
<223> OTHER INFORMATION: n = X = amino modifier C2 dT
<220> FEATURE:
<221> NAME/KEY: misc_feature
<222> LOCATION: (23)..(23)
<223> OTHER INFORMATION: n = X = amino modifier C2 dT
<220> FEATURE:
<221> NAME/KEY: misc_feature
<222> LOCATION: (27)..(27)
<223> OTHER INFORMATION: n = X = amino modifier C2 dT

<400> SEQUENCE: 66
taagatccag tagacgncca tanacanta                                29

<210> SEQ ID NO 67
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: n = X = amino modifier C2 dT
<220> FEATURE:
<221> NAME/KEY: misc_feature
<222> LOCATION: (7)..(7)
<223> OTHER INFORMATION: n = X = amino modifier C2 dT
<220> FEATURE:
<221> NAME/KEY: misc_feature
<222> LOCATION: (18)..(18)
<223> OTHER INFORMATION: n = X = amino modifier C2 dT

<400> SEQUENCE: 67
ngcaganaca gtaaacgncc atagacacag                               30

<210> SEQ ID NO 68
<211> LENGTH: 66
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(25)
<223> OTHER INFORMATION: N= U = deoxyuridine modified with the indole
      group of tryptophan
<220> FEATURE:
<221> NAME/KEY: misc_feature
<222> LOCATION: (33)..(33)
<223> OTHER INFORMATION: N= U = deoxyuridine modified with the indole
      group of tryptophan
<220> FEATURE:
<221> NAME/KEY: misc_feature
<222> LOCATION: (37)..(39)
<223> OTHER INFORMATION: N= U = deoxyuridine modified with the indole
      group of tryptophan
<220> FEATURE:
<221> NAME/KEY: misc_feature
<222> LOCATION: (42)..(42)
<223> OTHER INFORMATION: N= U = deoxyuridine modified with the indole
      group of tryptophan

<400> SEQUENCE: 68
ggtgtgctgt ggcagcgacg aatnncaagg gcntttnnnc tngcaatcgt tccgtgcggg    60
```

```
agcctg                                                                    66

<210> SEQ ID NO 69
<211> LENGTH: 66
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (28)..(28)
<223> OTHER INFORMATION: deoxyuridines modified with the indole
      group of tryptophan
<220> FEATURE:
<221> NAME/KEY: misc_feature
<222> LOCATION: (33)..(33)
<223> OTHER INFORMATION: deoxyuridines modified with the indole
      group of tryptophan
<220> FEATURE:
<221> NAME/KEY: misc_feature
<222> LOCATION: (37)..(39)
<223> OTHER INFORMATION: deoxyuridines modified with the indole
      group of tryptophan
<220> FEATURE:
<221> NAME/KEY: misc_feature
<222> LOCATION: (42)..(42)
<223> OTHER INFORMATION: deoxyuridines modified with the indole
      group of tryptophan
<220> FEATURE:
<221> NAME/KEY: misc_feature
<222> LOCATION: (44)..(44)
<223> OTHER INFORMATION: deoxyuridines modified with the indole
      group of tryptophan

<400> SEQUENCE: 69
ggtgtgctgt ggcagcgacg atcggttnca ttnccannnt tntntctcgt tccgtgcggg        60
agcctg                                                                    66
```